US010426574B2

(12) United States Patent
Raby et al.

(10) Patent No.: US 10,426,574 B2
(45) Date of Patent: Oct. 1, 2019

(54) COMPUTER SYSTEM-AIDED DESIGN OF DENTAL APPLIANCES

(71) Applicant: 3M INNOVATIVE PROPERTIES COMPANY, St. Paul, MN (US)

(72) Inventors: Richard E. Raby, Lino Lakes, MN (US); Oliver L. Puttler, La Crescenta, CA (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 263 days.

(21) Appl. No.: 15/539,198

(22) PCT Filed: Dec. 30, 2015

(86) PCT No.: PCT/US2015/068041
§ 371 (c)(1),
(2) Date: Jun. 23, 2017

(87) PCT Pub. No.: WO2016/109654
PCT Pub. Date: Jul. 7, 2016

(65) Prior Publication Data
US 2017/0367792 A1    Dec. 28, 2017

Related U.S. Application Data

(60) Provisional application No. 62/097,735, filed on Dec. 30, 2014, provisional application No. 62/097,733, filed on Dec. 30, 2014.

(51) Int. Cl.
*A61C 7/00* (2006.01)
*A61C 7/08* (2006.01)
(Continued)

(52) U.S. Cl.
CPC ............... *A61C 7/002* (2013.01); *A61C 7/08* (2013.01); *A61C 7/20* (2013.01); *A61C 7/36* (2013.01)

(58) Field of Classification Search
CPC ..................................................... A61C 7/00
See application file for complete search history.

(56) References Cited

U.S. PATENT DOCUMENTS 4,253,828 A * 3/1981 Coles ..................... A61C 7/00
433/6
4,299,568 A 11/1981 Crowley
(Continued)

FOREIGN PATENT DOCUMENTS

CN    103340690 A    10/2013
CN    104083223 A    10/2014
(Continued)

OTHER PUBLICATIONS

International Search Report for PCT International Application No. PCT/US2015/068041 dated May 4, 2016, 3 pages.

*Primary Examiner* — Cachet I Proctor

(57) ABSTRACT

A method includes receiving, with a computer system, a digital representation of a 3D tooth structure providing initial positions of one or more teeth of a patient, determining dimensions and shapes of a removable dental appliance, the dimensions and shapes being configured to reposition the one or more teeth from their initial positions to adjusted positions when the dental appliance is worn, and transmitting a representation of the dental appliance to a computer-aided manufacturing system. The dental appliance includes an appliance body configured to surround two or more teeth of the patient with a facial portion configured to register with facial sides of the surrounded teeth, and a lingual portion configured to register with lingual sides of the surrounded teeth. The appliance body is configured such that occlusal surfaces of the surrounded teeth of the patient are exposed when the removable dental appliance is worn by the patient.

17 Claims, 15 Drawing Sheets

(51) Int. Cl.
*A61C 7/20* (2006.01)
*A61C 7/36* (2006.01)

(56) References Cited

U.S. PATENT DOCUMENTS

| | | | |
|---|---|---|---|
| 4,976,614 A * | 12/1990 | Tepper | A61C 7/00 433/18 |
| 5,096,416 A | 3/1992 | Hulsink | |
| 5,242,304 A | 9/1993 | Truax et al. | |
| 5,536,169 A | 7/1996 | Yousefian | |
| 5,607,300 A | 3/1997 | Tepper | |
| 6,135,767 A * | 10/2000 | Kesling | A61C 7/00 433/21 |
| 6,152,731 A * | 11/2000 | Jordan | A61C 13/0003 433/69 |
| 6,217,334 B1 * | 4/2001 | Hultgren | A61C 9/0006 433/215 |
| 6,350,120 B1 * | 2/2002 | Sachdeva | A61C 7/00 433/24 |
| 6,554,611 B2 | 4/2003 | Chishti et al. | |
| 6,629,840 B2 | 10/2003 | Chishti et al. | |
| 6,766,802 B1 | 7/2004 | Keropian | |
| 6,845,175 B2 | 1/2005 | Kopelman et al. | |
| 7,027,642 B2 | 4/2006 | Rubbert et al. | |
| 7,234,937 B2 | 6/2007 | Sachdeva et al. | |
| 7,661,955 B2 | 2/2010 | Da Cruz | |
| 7,731,495 B2 | 6/2010 | Eisenberg et al. | |
| 8,062,031 B2 | 11/2011 | Inman | |
| 8,070,487 B2 | 12/2011 | Chishti et al. | |
| 8,194,067 B2 | 6/2012 | Raby et al. | |
| 8,359,114 B2 | 1/2013 | Steingart | |
| 8,469,706 B2 * | 6/2013 | Kuo | A61C 7/08 433/18 |
| 8,491,306 B2 | 7/2013 | Raby et al. | |
| 8,738,165 B2 | 5/2014 | Cinader, Jr. et al. | |
| 8,827,697 B2 | 9/2014 | Cinader, Jr. et al. | |
| 8,882,499 B2 * | 11/2014 | White | A61C 7/00 433/18 |
| 8,897,902 B2 | 11/2014 | See et al. | |
| 9,408,675 B2 * | 8/2016 | Knopp | A61C 7/00 |
| 2001/0002310 A1 * | 5/2001 | Chishti | A61C 7/00 433/24 |
| 2001/0041320 A1 | 11/2001 | Phan et al. | |
| 2002/0192617 A1 | 12/2002 | Phan | |
| 2003/0190576 A1 | 10/2003 | Phan | |
| 2004/0029068 A1 | 2/2004 | Sachdeva et al. | |
| 2006/0003292 A1 | 1/2006 | Lauren et al. | |
| 2006/0078840 A1 | 4/2006 | Robson | |
| 2006/0110698 A1 | 5/2006 | Robson | |
| 2007/0031791 A1 | 2/2007 | Cinader, Jr. et al. | |
| 2007/0087300 A1 | 4/2007 | Willison et al. | |
| 2010/0082148 A1 | 4/2010 | Cinader, Jr. | |
| 2010/0086890 A1 | 4/2010 | Kuo | |
| 2011/0027743 A1 * | 2/2011 | Cinader, Jr. | A61C 7/006 433/11 |
| 2012/0214121 A1 * | 8/2012 | Greenberg | A61B 5/0088 433/24 |
| 2012/0219922 A1 | 8/2012 | Matty et al. | |
| 2013/0095446 A1 | 4/2013 | Andreiko et al. | |
| 2013/0266906 A1 | 10/2013 | Soo | |
| 2013/0323665 A1 | 12/2013 | Dinh et al. | |
| 2014/0124968 A1 | 5/2014 | Kim | |
| 2014/0180463 A1 | 6/2014 | Chishti et al. | |
| 2016/0008098 A1 | 1/2016 | Dolfi | |
| 2016/0081767 A1 | 3/2016 | Metcalf | |
| 2016/0278884 A1 | 9/2016 | Hung | |
| 2017/0079747 A1 | 3/2017 | Graf | |

FOREIGN PATENT DOCUMENTS

| | | |
|---|---|---|
| CN | 203935287 U | 11/2014 |
| CN | 104224330 A | 12/2014 |
| EP | 2754407 | 7/2014 |
| RU | 2017655 | 8/2001 |
| RU | 2171654 | 8/2001 |
| WO | WO 01/80762 | 11/2001 |
| WO | WO 2007/084727 | 7/2007 |
| WO | WO 2014/106676 | 7/2014 |

* cited by examiner

COMPUTER SYSTEM-AIDED DESIGN OF DENTAL APPLIANCES

CROSS REFERENCE TO RELATED APPLICATIONS

This application is a national stage filing under 35 U.S.C. 371 of PCT/US2015/068041, filed Dec. 30, 2015, which claims the benefit of U.S. Provisional Application Nos. 62/097,735, filed Dec. 30, 2014, and 62/097,733, filed Dec. 30, 2014, the disclosures of which are incorporated by reference in their entireties herein.

TECHNICAL FIELD

This disclosure relates to orthodontics and, more particularly, computer-based methods for assisting orthodontic diagnosis and treatment.

BACKGROUND

The field of orthodontics is concerned with repositioning a patient's teeth for improved function and aesthetic appearance. For example, orthodontic treatment often involves the use of tiny slotted appliances, known as brackets, which are generally fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth. The archwire and appliances are commonly referred to as "braces." Orthodontic treatment may also be implemented through the use of clear, plastic tooth positioning trays or other functional appliances.

The practice of orthodontics has traditionally relied on manual steps, such as the selection of proper appliances for the particular patient, placement of appliances in the mouth, and adjustment of appliances throughout treatment. More recently, advancement in technology has allowed some of these steps to be assisted through the use of computers. For example, computers can be used to guide the acquisition of data representing the teeth arrangement of an individual patient. Such data can then be used to visualize the patient's dentition to diagnose and assist in orthodontic treatment planning at any stage of treatment. Furthermore, these data can be used in manufacturing appliances, such as brackets, that are customized to the patient.

SUMMARY

This disclosure relates to removable dental appliances for dental realignment and/or maintenance and devices, systems, and techniques for designing, manufacturing and using removable dental appliances. In some examples, the removable dental appliances provide substantially exposed occlusal surfaces of the patient's teeth when worn by a patient. A removable dental appliance providing substantially exposed occlusal surfaces may provide a number of advantages as compared to removable dental appliances that substantially occlude the teeth of a patient, such as improved patient comfort, reduced visibility of the dental appliance, reduced tarter growth due to increased air and saliva flow between teeth, and the ability for a patient to eat or drink to some degree without having to remove the dental appliance.

In one example, this disclosure is directed to a method comprising receiving, with a computer system, a digital representation of a three-dimensional (3D) tooth structure of a patient, the tooth structure providing initial positions of one or more teeth of the patient, determining, with the computer system, dimensions and shapes of a removable dental appliance for the patient, the dimensions and shapes of the removable dental appliance being configured to reposition the one or more teeth of the patient from their initial positions to adjusted positions when the removable dental appliance is worn by the patient, and transmitting, with the computer system, a representation of the removable dental appliance to a computer-aided manufacturing system. The removable dental appliance comprises an appliance body configured to surround two or more teeth of the patient. The appliance body includes a facial portion configured to register with facial sides of the surrounded teeth, and a lingual portion configured to register with lingual sides of the surrounded teeth. The appliance body is configured such that occlusal surfaces of the surrounded teeth of the patient are exposed when the removable dental appliance is worn by the patient.

In addition, this disclosure is further directed to a computer-readable storage medium that stores computer system-executable instructions that, when executed, configure a processor to perform such a method.

In an additional example, this disclosure is directed to a computer-readable storage medium that stores computer-executable instructions that, when executed, configure a processor to receive a digital representation of a three-dimensional (3D) tooth structure of a patient, the tooth structure providing initial positions of one or more teeth of the patient, determine dimensions and shapes of a removable dental appliance for the patient, the dimensions and shapes of the removable dental appliance being configured to reposition the one or more teeth of the patient from their initial positions to adjusted positions when the removable dental appliance is worn by the patient, and transmit a representation of the removable dental appliance to a computer-aided manufacturing system. The removable dental appliance comprises an appliance body configured to surround two or more teeth of the patient. The appliance body includes a facial portion configured to register with facial sides of the surrounded teeth, and a lingual portion configured to register with lingual sides of the surrounded teeth. The appliance body is configured such that occlusal surfaces of the surrounded teeth of the patient are exposed when the removable dental appliance is worn by the patient.

In another example, this disclosure is directed to a computer system comprising one or more databases storing a digital representation of a three-dimensional (3D) tooth structure of a patient, the tooth structure providing initial positions of one or more teeth of the patient, and one or more processors. The one or more processors being configured to access the digital representation of the 3D tooth structure, determine dimensions and shapes of a removable dental appliance for the patient, the dimensions and shapes of the removable dental appliance being configured to reposition the one or more teeth of the patient from their initial positions to adjusted future positions when the removable dental appliance is worn by the patient, and transmit a representation of the removable dental appliance to a computer-aided manufacturing system. The removable dental appliance comprises an appliance body configured to surround two or more teeth of the patient. The appliance body includes a facial portion configured to register with facial sides of the surrounded teeth, and a lingual portion configured to register with lingual sides of the surrounded teeth. The appliance body is configured such that occlusal surfaces of the surrounded teeth of the patient are exposed when the removable dental appliance is worn by the patient.

In a further example, this disclosure is directed to a removable dental appliance configured to reposition one or more teeth of a patient. The removable dental appliance includes comprising an appliance body forming an active band configured to surround two or more teeth of the patient. The appliance body includes a facial portion configured to register with facial sides of the surrounded teeth, and a lingual portion configured to register with lingual sides of the surrounded teeth. The facial portion of the appliance body and the lingual portion of the appliance body form receptacles. Each receptacle is configured to accept at least one of the surrounded teeth. The receptacles separate the facial portion from the lingual portion at least along an anterior portion of the appliance body. The active band is configured such that occlusal surfaces of the surrounded teeth of the patient are exposed when the removable dental appliance is worn by the patient with the surrounded teeth positioned within the active band of the appliance body.

In another example, this disclosure is directed to a system including an ordered set of removable dental appliances configured to reposition one or more teeth of a patient, each removable dental appliance in the set of removable dental appliances including an appliance body forming an active band configured to surround two or more teeth of the patient. The appliance body includes a facial portion configured to register with facial sides of the surrounded teeth, and a lingual portion configured to register with lingual sides of the surrounded teeth. The facial portion of the appliance body and the lingual portion of the appliance body form receptacles. Each receptacle is configured to accept at least one of the surrounded teeth. The active band separates the facial portion from the lingual portion at least along an anterior portion of the appliance body. The active band is configured such that occlusal surfaces of the surrounded teeth of the patient are exposed when the removable dental appliance is worn by the patient with the surrounded teeth positioned within the active band of the appliance body.

The details of one or more examples of this disclosure are set forth in the accompanying drawings and the description below. Other features, objects, and advantages of this disclosure will be apparent from the description and drawings, and from the claims.

DETAILED DESCRIPTION

Figure 1:
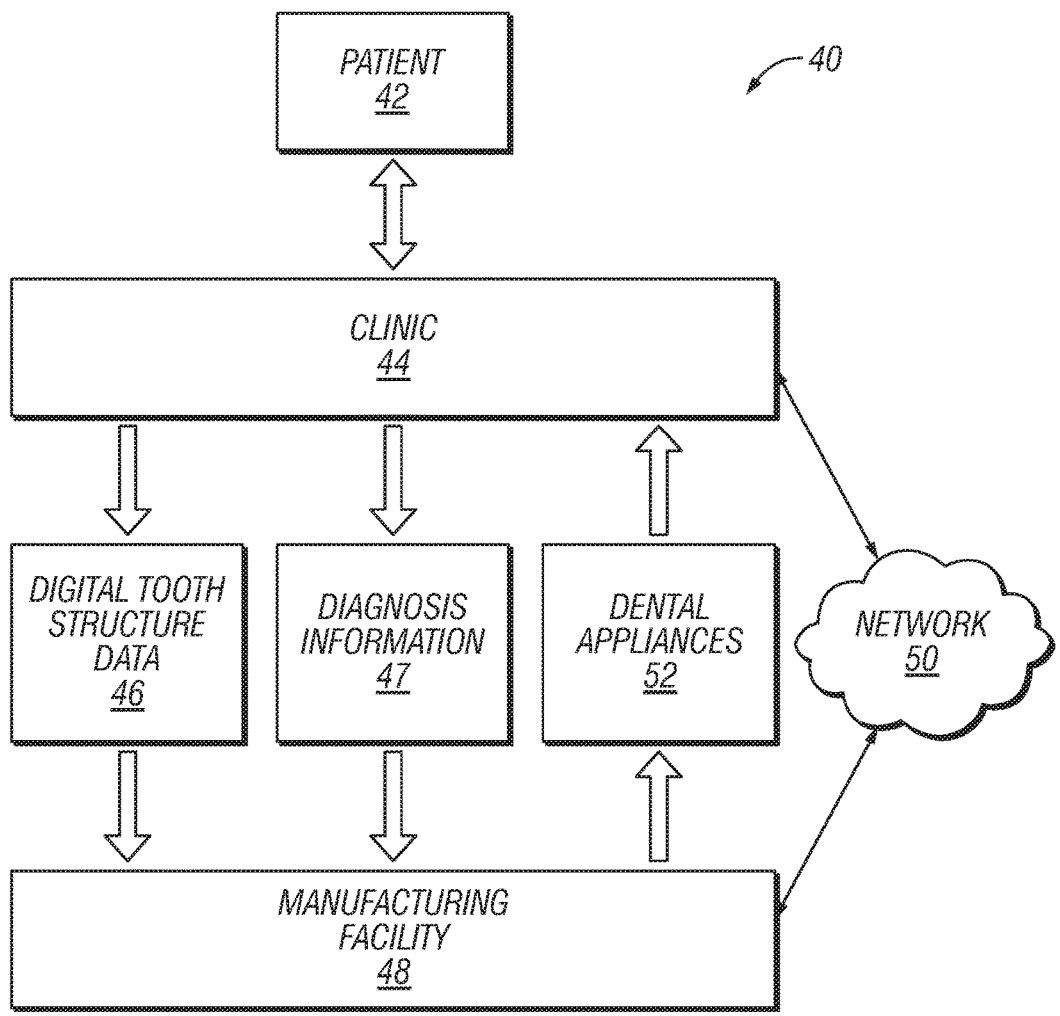
FIG. 1 is a block diagram illustrating an example computer environment in which a clinic and manufacturing facility communicate information throughout a dental appliance manufacturing process.

FIG. 1 is a block diagram illustrating an example computer environment 40 in which clinic 44 and manufacturing facility 48 communicate information throughout a manufacturing process of a set of removable dental appliances 52 for patient 42. Initially, an orthodontic practitioner of clinic 44 generates one or more images of a dental structure of patient 42 using any suitable imaging technique and generates digital dental structure data 46 (e.g., a digital representation of patient's 42 tooth structure). For example, the practitioner may generate X-RAY images that can be digitally scanned. Alternatively, the practitioner may capture digital images of the patient tooth structure using, for example, conventional computed tomography (CT), laser scanning, intra-oral scanning, CT scans of dental impressions, scans of dental casts poured from impressions, ultrasound instrumentation, magnetic resonance imaging (MRI), or any other suitable method of 3D data acquisition. In other embodiments, the digital images may be provided using a hand-held intra-oral scanner such as the intra-oral scanner using active wavefront sampling developed by Brontes Technologies, Inc. (Lexington, Mass.) and described in PCT Publication No. WO 2007/084727 (Boerjes, et al.), which is incorporated by reference herein. Alternatively, other intra-oral scanners or intra-oral contact probes may be used. As another option, the digital structure data 48 may be provided by scanning a negative impression of the patient's teeth. As still another option, the digital structure data 48 may be provided by imaging a positive physical model of the patient's teeth or by using a contact probe on a model of the patient's teeth. The model used for scanning may be made, for example, by casting an impression of a patient's dentition from a suitable impression material such as alginate or polyvinylsiloxane (PVS), pouring a casting material (such as orthodontic stone or epoxy resin) into the impression, and allowing the casting material to cure. Any suitable scanning technique may be used for scanning the model, including those described above. Other possible scanning methods are described in U.S. Patent Publication No. 2007/0031791 (Cinader et al.), which is incorporated by reference herein.

In addition to providing digital images by scanning the exposed surfaces of the teeth, it is possible to image hidden features of the dentition, such as the roots of the patient's teeth and the patient's jaw bones. In some embodiments, the digital tooth structure data is formed by providing several 3D images of these features and subsequently "stitching" them together. These different images need not be provided using the same imaging technique. For example, a digital image of teeth roots provided with a CT scan may be integrated with a digital image of the teeth crowns provided with an intraoral visible light scanner. Scaling and registering of 2D dental images with 3D dental images is described in U.S. Pat. No. 6,845,175 (Kopelman, et al.), which is incorporated by reference herein, and U.S. Patent Publication No. 2004/0029068 (Badura et al.), which is also incorporated by reference herein. Issued U.S. Pat. No. 7,027,642 (Imgrund et al.), which is incorporated by reference herein, and U.S. Pat. No. 7,234,937 (Sachdeva, et al.), which is also incorporated by reference herein, describe using techniques of integrating digital images provided from various 3D sources. Accordingly, the term "imaging" as it is used herein is not limited to normal photographic imaging of visually apparent structures, but includes imaging of dental structures that are hidden from view. The dental structure may include, but is not limited to, any portion of crowns and/or roots of one or more teeth of a dental arch, gingiva, periodontal ligaments, alveolar bone, cortical bone, implants, artificial crowns, bridges, veneers, dentures, orthodontic appliances, or any structure that could be considered part of the dentition before, during, or after treatment.

In order to generate digital tooth structure data 46, a computer must transform raw data from the imaging systems into usable digital models. For example, for raw data representing the shapes of teeth received by a computer, the raw data is often little more than a point cloud in 3D space. Typically, this point cloud is surfaced to create 3D object models of the patient's dentition, including one or more teeth, gingival tissue, and other surrounding oral structure. In order for this data to be useful in orthodontic diagnosis and treatment, the computer may "segment" dentition surfaces to produce one or more discrete, movable 3D tooth object models representing individual teeth. The computer may further separate these tooth models from the gingiva into separate objects.

Segmentation allows a user to characterize and manipulate the teeth arrangement as a set of individual objects. Advantageously, the computer may derive diagnostic information such as arch length, bite setting, and even American Board of Orthodontics (ABO) objective grading from these models. As a further benefit, the digital orthodontic setups may provide flexibility in the manufacturing process. By replacing physical processes with digital processes, the data acquisition step and data manipulation steps can be executed at separate locations without the need to transport stone models or impressions from one location to another. Reducing or eliminating the need for shipping physical objects back and forth can result in significant cost savings to both customers and manufacturers of customized appliances.

After generating digital dental structure data 46, clinic 44 may store digital dental structure data 46 within a patient record in a database. Clinic 44 may, for example, update a local database having a plurality of patient records. Alternatively, clinic 44 may remotely update a central database (optionally within manufacturing facility 48) via network 50. After digital tooth structure data 46 is stored, clinic 44 electronically communicates digital dental structure data 46 to manufacturing facility 48. Alternatively, manufacturing facility 48 may retrieve digital dental structure data 46 from the central database.

Clinic 44 may also forward prescription data 47 conveying general information regarding a practitioner's diagnosis and treatment plan for patient 42 to manufacturing facility 48. In some examples, prescription data 47 may be more specific. For example, digital dental structure data 46 may be a digital representation of the dental structure of patient 42, and the practitioner of clinic 44 may review the digital representation and indicate desired movement, spacing or final positions of individual teeth of patient 42 following treatment with the set of removable dental appliances 52 prior to forwarding digital dental structure data 46 to manufacturing facility 48. Manufacturing facility 48 may be located off-site, or located with clinic 44.

For example, each clinic 44 may include its own equipment for manufacturing facility 48 such that a treatment plan and digital design may be performed entirely by a clinical practitioner, or an assistant, in the clinical setting, using software installed locally. The manufacturing may be performed in the clinic, as well, by using a 3D printer (or by other methods of additive manufacturing). A 3D printer allows manufacturing of intricate features of a dental appliance or a physical representation of the dental structure of patient 42 through additive printing. The 3D printer may use iterative digital designs of original dental structure of patient 42 as well as a desired dental structure of patient 42 to produce multiple digital appliances and/or digital appliance patterns customized to produce the desired dental structure of patient 42. Manufacturing may include post-processing to remove uncured resin and remove support structures, or to assemble various components, which may also be necessary and could also be performed in a clinical setting.

Manufacturing facility 48 utilizes digital dental structure data 46 of patient 42 to construct the set of removable dental appliances 52 in order to reposition teeth of patient 42. Sometime thereafter, manufacturing facility 48 forwards the set of removable dental appliances 52 to clinic 44 or, alternatively, directly to patient 42. For example, the set of removable dental appliances 52 may be an ordered set of removable dental appliances. Patient 42 then wears the removable dental appliances in the set of removable dental appliances 52 sequentially over time according to a prescribed schedule in order to reposition the teeth of patient 42. For example, patient 42 may wear each removable dental appliance in the set of removable dental appliances 52 for a period of between about 2 weeks and about 12 weeks, such as between about 3 weeks and about 10 weeks or between about 4 weeks and about 8 weeks. Optionally, patient 42 may return to clinic 44 for periodic monitoring of the progress of the treatment with removable dental appliances 52.

During such periodic monitoring, a clinician may adjust the prescribed schedule of patient 42 for wearing the removable dental appliances in the set of removable dental appliances 52 sequentially over time. Monitoring generally includes visual inspection of the teeth of patient 42 and may also include imaging to generate digital tooth structure data. In some relatively uncommon circumstances, the clinician may decide to interrupt the treatment of patient 42 with the set of removable dental appliances 52, for example, by sending the newly generated digital dental structure data to manufacturing facility 48 in order to produce a new set of removable dental appliances. In the same or different examples, the clinician may send newly generated digital dental structure data to manufacturing facility 48 following the completion of the prescribed schedule of the treatment with removable dental appliances 52. In addition, following the completion of the prescribed schedule of the treatment with removable dental appliances 52, the clinician may request a new set of removable dental appliances from manufacturing facility 48 to continue treatment of patient 42.

Figure 2:
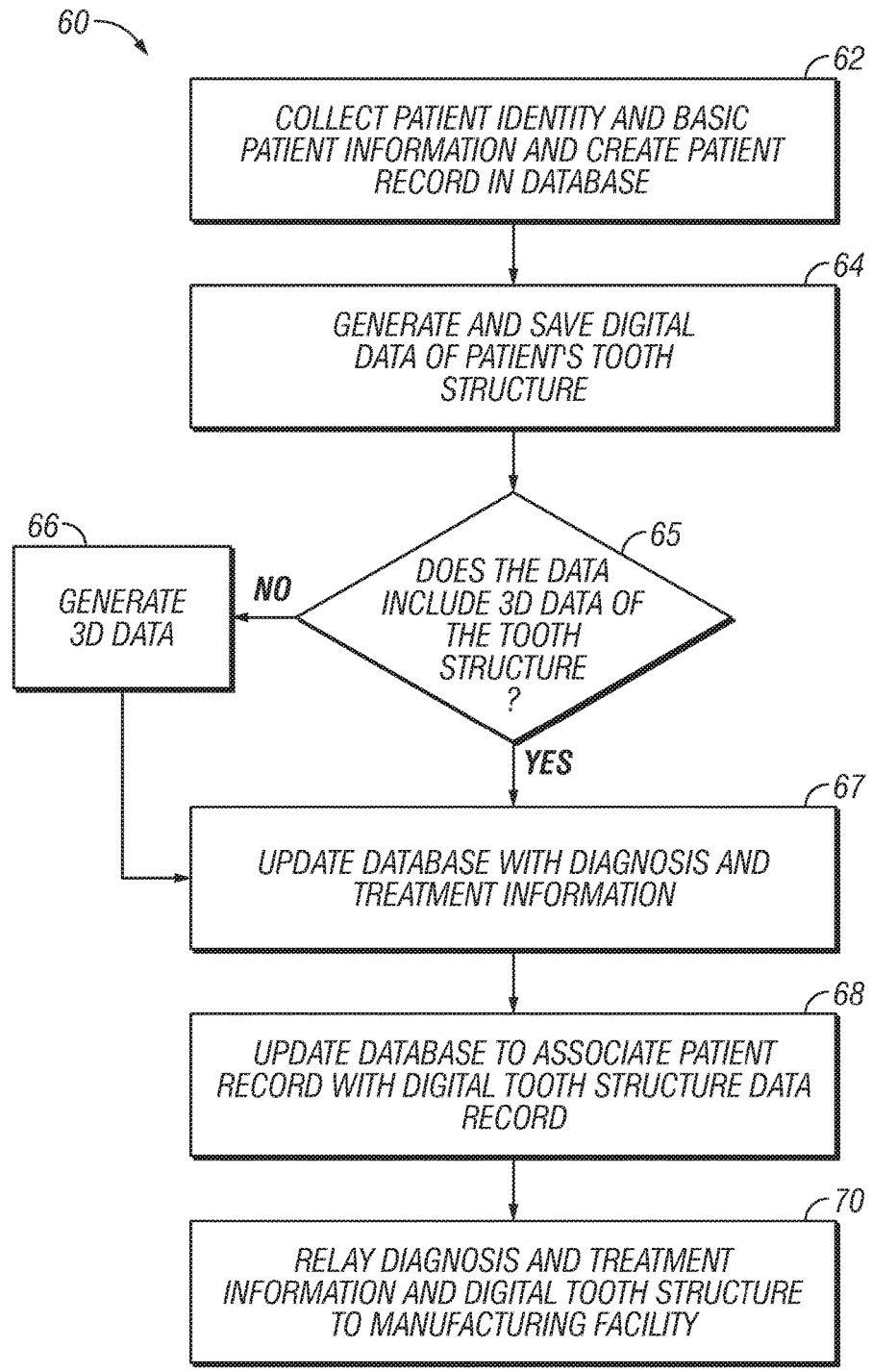
FIG. 2 is a flow diagram illustrating a process conducted at the clinic in accordance with one example of this disclosure.

FIG. 2 is a flow diagram illustrating process 60 conducted at clinic 44 in accordance with one example of this disclosure. Initially, a practitioner at clinic 44 collects patient identity and other information from patient 42 and creates a patient record (62). As described, the patient record may be located within clinic 44 and optionally configured to share data with a database within manufacturing facility 48. Alternatively, the patient record may be located within a database at manufacturing facility 48 that is remotely accessible to clinic 44 via network 50 or within a database that is remotely accessible by both manufacturing facility 48 and clinic 44.

Next, digital data 46 of the dental structure of patient 42 may be generated using any suitable technique (64), to thereby create a virtual dental structure. Digital data 46 may be comprised of a two-dimensional (2D) image and/or a three-dimensional (3D) representation of the dental structure.

In one example, 3D representations of a dental structure are generated using a cone beam computerized tomography (CBCT) scanner, such as an i-CAT 3D dental imaging device, which is available from Imaging Sciences International, LLC; 1910 N Penn Road, Hatfield, Pa. Clinic 44 stores the 3D data 46 (in the form of radiological images) generated from the CBCT scanner in the database located within clinic 44, or alternatively, within manufacturing facility 48. The computing system processes the digital data 46 from the CBCT scanner, which may be in the form of a plurality of slices, to compute a digital representation of the tooth structure that may be manipulated within the 3D modeling environment.

If 2D radiological images are used (65), then the practitioner may further generate 3D digital data (66). The 3D data 46 may be produced by, for example, forming and subsequently digitally scanning a physical impression or casting of the tooth structure of patient 42. For example, a physical impression or casting of a dental arch of patient 42 may be scanned using a visible light scanner, such as an OM-3R scanner available from Laser Design, Inc. of Minneapolis, Minn. Alternatively, the practitioner may generate the 3D data 46 of the occlusal service by use of an intra-oral scan of the dental arch of patient 42, or existing 3D tooth data. In one example, the method of forming a digital scan from a casting or an impression described in U.S. Pat. No. 8,491,306, titled, "REGISTERING PHYSICAL AND VIRTUAL TOOTH STRUCTURES WITH PEDESTALS," and issued on Jul. 23, 2013, may be used. U.S. Pat. No. 8,491,306 is herein incorporated by reference in its entirety. In the same or different examples, techniques for defining a virtual tooth surface and virtual tooth coordinate system as described in U.S. Pat. No. 8,897,902, titled ORTHODONTIC DIGITAL SETUPS," and published on Nov. 25, 2014 may be used. U.S. Pat. No. 8,897,902 is herein incorporated by reference in its entirety. In any case, the digital data are digitally registered within the 3D modeling environment to form a composite digital representation of a tooth structure, which may include the tooth roots as well as the occlusal surfaces.

In one example, 2D radiological images and the 3D digital data for the occlusal surface of the dental arch are registered by first attaching registration markers (e.g., fiducial markers or a pedestal having known geometry) to the tooth structure of patient 42 prior to generating both the radiological images and the 3D digital scan. Thereafter, the digital representation of the registration markers within the 2D radiological image and the 3D digital data may be aligned within a 3D modeling environment using registration techniques described in U.S. Pat. No. 8,491,306.

In another example, 3D digital data of the tooth structure is generated by combining two 3D digital representations of the tooth structure. For example, a first 3D digital representation may be a relatively low resolution image of the roots obtained from a CBCT scanner (e.g., an i-CAT 3D dental imaging device) and the second 3D digital representation may be a relatively high resolution image of the crowns of the teeth obtained from an industrial CT scan of an impression or a visible light (e.g., laser) scan of a casting of the dental arch of the patient. The 3D digital representations may be registered using a software program that enables the 3D representations to be manipulated within a computer environment (e.g., Geomagic Studio software, available from 3D Systems, Inc.; 333 Three D Systems Circle, Rock Hill, S.C.), or alternatively, registration techniques described in U.S. Pat. No. 8,491,306 may be used.

Next, a computer system executing 3D modeling software renders a resultant digital representation of the tooth structure, including the occlusal surface as well as the root structure of the patient's dental arch. Modeling software provides a user interface that allows the practitioner to manipulate digital representations of the teeth in 3D space relative to the digital representation of the patient's dental arch. By interacting with the computer system, the practitioner generates treatment information, such as by selecting indications of the desired final positions or the teeth of patient 42 (67).

Once the practitioner has finished conveying general information regarding a diagnosis and treatment plan within the 3D environment, the computer system updates the database associated with the patient record to record the prescription data 47 conveying general information regarding a diagnosis and treatment plan as specified by the practitioner (68). Thereafter, the prescription data 47 is relayed to manufacturing facility 48 in order for manufacturing facility 48 to construct one or more removable dental appliances, such as removable dental appliances 52 (70).

Although described with respect to an orthodontic practitioner located at an orthodontic clinic, one or more of the steps discussed with respect to FIG. 2 may be performed by a remote user, such as a user located at manufacturing facility 48. For example, the orthodontic practitioner may only send radiological image data and an impression or casting of the patient to manufacturing facility 48, where a user interacts with a computer system to develop a treatment plan within a 3D modeling environment. Optionally, a digital representation of the treatment plan within the 3D modeling environment may then be transmitted to the orthodontic practitioner of clinic 44, who may review the treatment plan and either send back his or her approval, or indicate desired changes.

Figure 3:
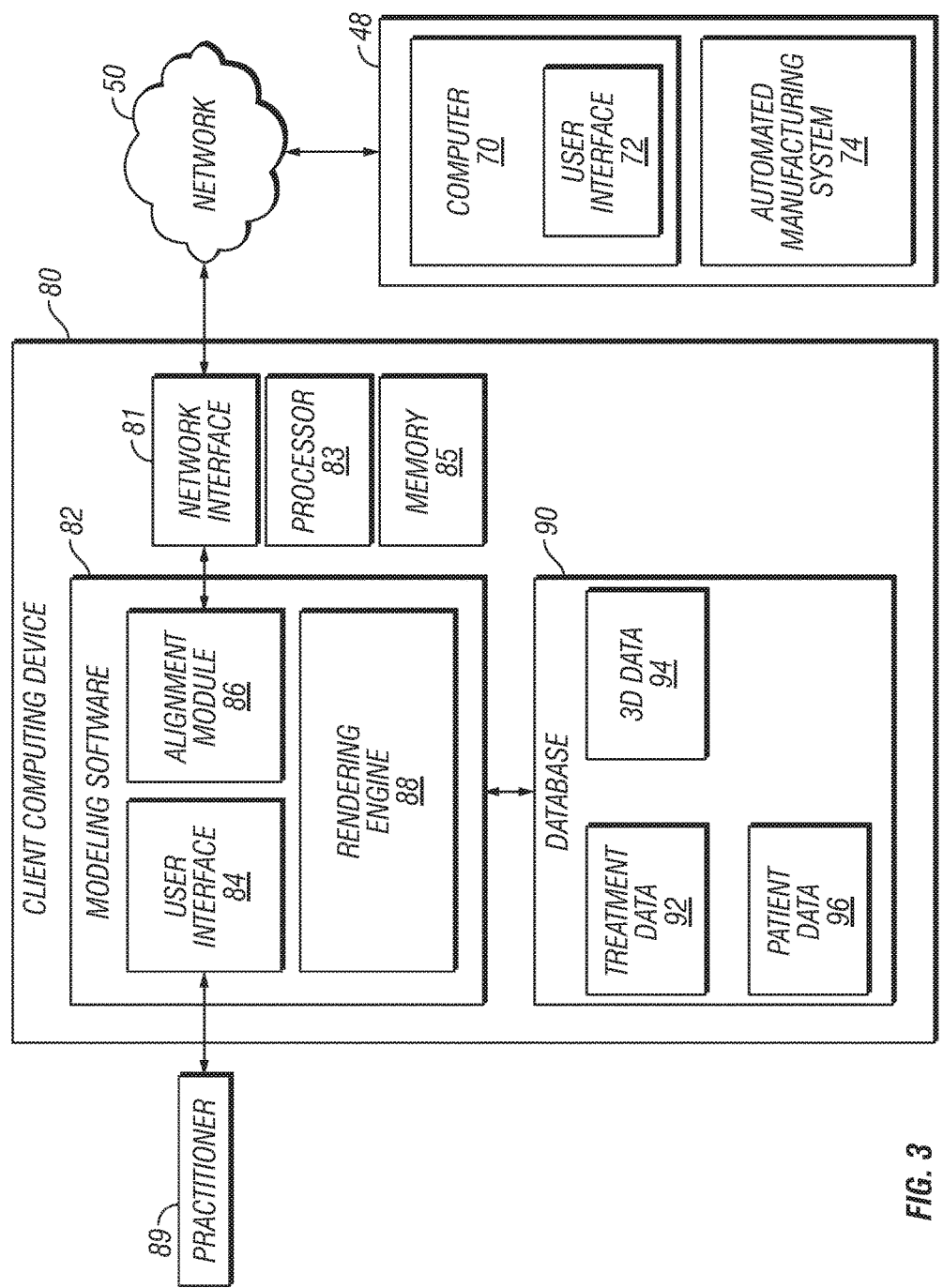
FIG. 3 is a block diagram illustrating an example of a client computing device connected to a manufacturing facility via a network.

FIG. 3 is a block diagram illustrating an example of a client computing device 80 connected to manufacturing facility 48 via network 50. In the illustrated example, client computing device 80 provides an operating environment for modeling software 82. Modeling software 82 presents a modeling environment for modeling and depicting the 3D representation of the teeth of patient 42. In the illustrated example, modeling software 82 includes user interface 84, alignment module 86, and rendering engine 88.

User interface 84 provides a graphical user interface (GUI) that visually displays the 3D representation of patient's 42 teeth. In addition, user interface 84 provides an interface for receiving input from practitioner 89 of clinic 44 (FIG. 1), e.g., via a keyboard and a pointing device, for manipulating patient's 42 teeth within the modeled dental arch.

Modeling software 82 may be accessible to manufacturing facility 48 via network interface 81. Modeling software 82 interacts with database 90 to access a variety of data, such as treatment data 92, 3D data 94 relating to the tooth structure of patient 42, and patient data 96. Database 90 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS) or object relational (ORDBMS) database management system. The data may, for example, be stored within a single relational database, such as SQL Server from Microsoft Corporation. Although illustrated as local to client computer device 80, database 90 may be located remote from the client computing device and coupled to the client computing device via a public or private network, e.g., network 50.

Treatment data 92 describes a diagnosis and or repositioning information of the teeth of patient 42 selected by practitioner 89 and positioned within the 3D modeling environment.

Patient data 96 describes a set of one or more patients, e.g., patient 42, associated with practitioner 89. For example, patient data 96 specifies general information, such as a name, birth date, and a dental history, for each patient.

Rendering engine 88 accesses and renders 3D data 94 to generate the 3D view presented to practitioner 89 by user interface 84. More specifically, 3D data 94 includes information defining the 3D objects that represent each tooth (optionally including roots), and jaw bone within the 3D environment. Rendering engine 88 processes each object to render a 3D triangular mesh based on viewing perspective of practitioner 89 within the 3D environment. User interface 84 displays the rendered 3D triangular mesh to practitioner 89, and allows practitioner 89 to change viewing perspectives and manipulate objects within the 3D environment.

U.S. Pat. No. 8,194,067, titled, "PLANAR GUIDES TO VISUALLY AID ORTHODONTIC APPLIANCE PLACEMENT WITHIN A THREE-DIMENSIONAL (3D) ENVIRONMENT," issued on Jun. 5, 2012, and U.S. Pat. No. 7,731,495, titled, "USER INTERFACE HAVING CROSS SECTION CONTROL TOOL FOR DIGITAL ORTHODONTICS," issued on Jun. 8, 2010, describe other examples for computer systems and 3D modeling software having user interfaces that may be used with the techniques described herein, each of which are incorporated by reference in their entireties.

Client computing device 80 includes processor 83 and memory 85 in order to store and execute modeling software 82. Memory 85 may represent any volatile or non-volatile storage elements. Examples include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include non-volatile storage, such as a hard-disk, magnetic tape, a magnetic or optical data storage media, a compact disk (CD), a digital versatile disk (DVD), a Blu-ray disk, and a holographic data storage media.

Processor 83 represents one or more processors such as a general-purpose microprocessor, a specially designed processor, an application specific integrated circuit (ASIC), a field programmable gate array (FPGA), a collection of discrete logic, or any type of processing device capable of executing the techniques described herein. In one example, memory 214 may store program instructions (e.g., software instructions) that are executed by processor 212 to carry out the techniques described herein. In other examples, the techniques may be executed by specifically programmed circuitry of processor 83. In these or other ways, processor 83 may be configured to execute the techniques described herein.

Client computing device 80 is configured to send a digital representation of a 3D tooth structure of a patient, and optionally, treatment data 92 and/or patient data 96 to computer 70 of manufacturing facility 48 via network 50. Computer 70 includes user interface 72. User interface 72 provides a GUI that visually displays the 3D representation of the digital model of teeth. In addition, user interface 72 provides an interface for receiving input from a user, e.g., via a keyboard and a pointing device, for manipulating a patient's teeth within the digital representation of the 3D tooth structure of the patient.

Computer 70 may further be configured to determine dimensions and shapes of a set of removable dental appliances for the patient, the dimensions and shapes of the removable dental appliance being configured to reposition the one or more teeth of the patient from their initial positions to adjusted positions when the removable dental appliances are worn by the patient. Computer 70 may provide the dimensions and shapes of the set of removable dental appliances for the patient to automated manufacturing system 74 for production of the set of removable dental appliances.

Client computing device 80 and computer 70 are merely conceptual representations of an example computer system. In some examples, the functionalities described with respect to of client computing device 80 and/or computer 70 may be combined into a single computing device or distributed among multiple computing devices within a computer system. For example, cloud computing may be used for digital design of dental appliances described herein. In one example, the digital representations of tooth structures are received at one computer at the clinic, while a different computer, such as computer 70, is used to determine the shapes and dimensions of a dental appliance. In addition, it may not be necessary for that different computer, such as computer 70, to receive all of the same data in order for it determine shapes and dimensions. Shapes and dimensions may be determined, at least in part, based on knowledge derived through analysis of historical cases or virtual models of exemplary cases, without receiving a complete 3D representation of the case in question. In such an example, data transmitted between client computing device 80 and computer 70, or otherwise utilized to design a custom dental appliance may be significantly less than the complete data set representing a complete digital dental model of a patient.

Figure 4A:
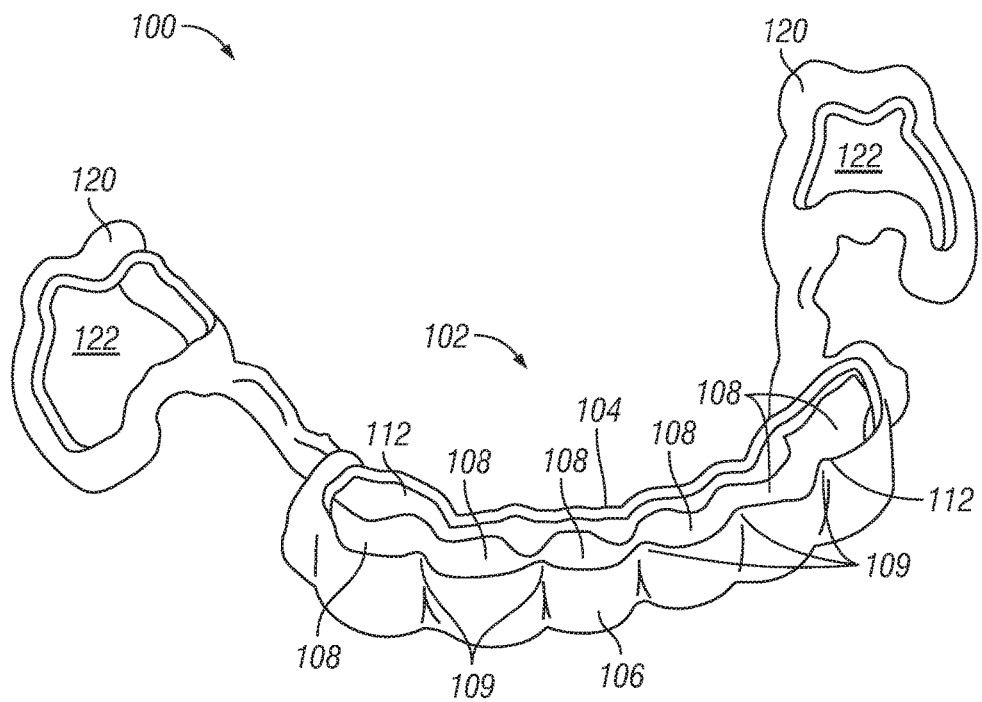
FIGS. 4A and 4B illustrate an example removable dental appliance providing exposed occlusal surfaces when worn by a patient.
Figure 4B:
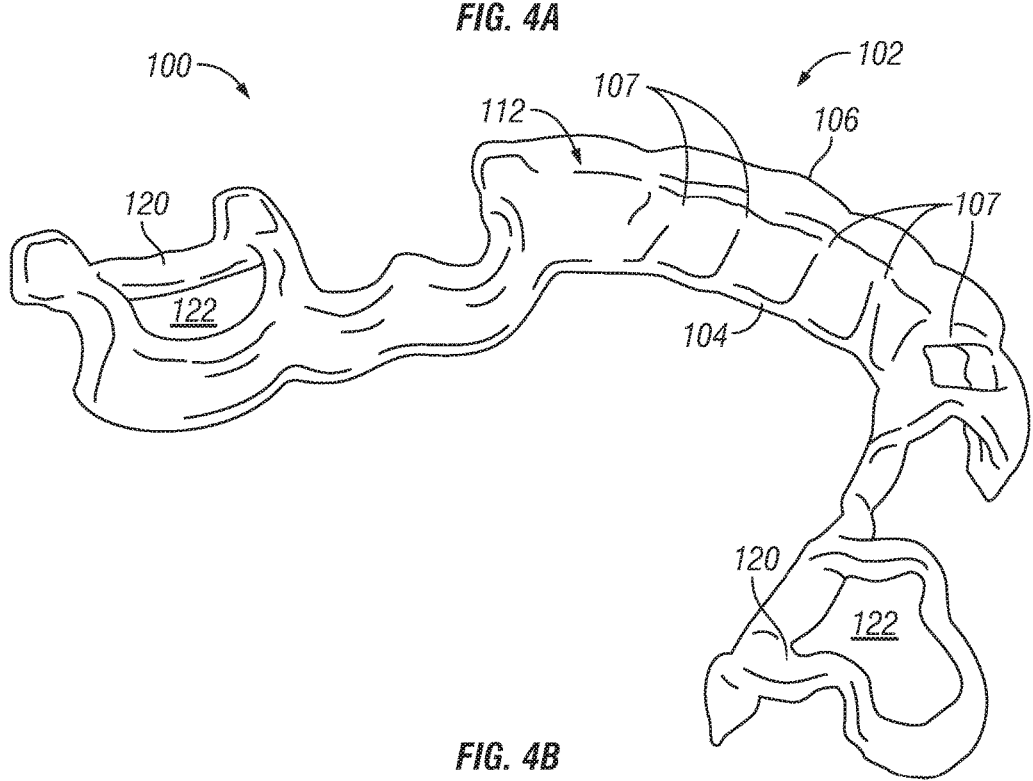
Figure 5A:
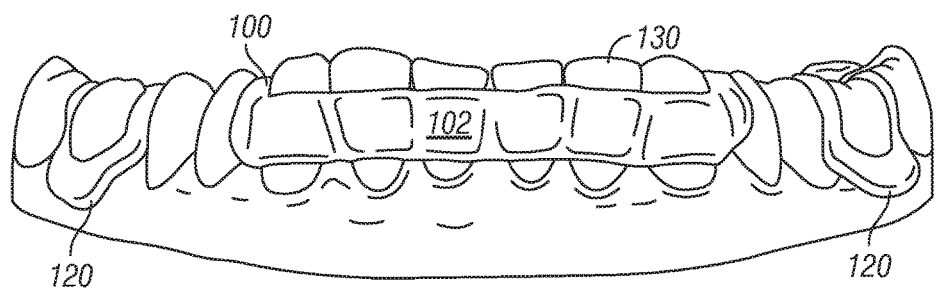
FIGS. 5A and 5B illustrate a 3D digital model of a removable dental appliance providing exposed occlusal surfaces in combination with a 3D digital model of the teeth of a patient.
Figure 5B:
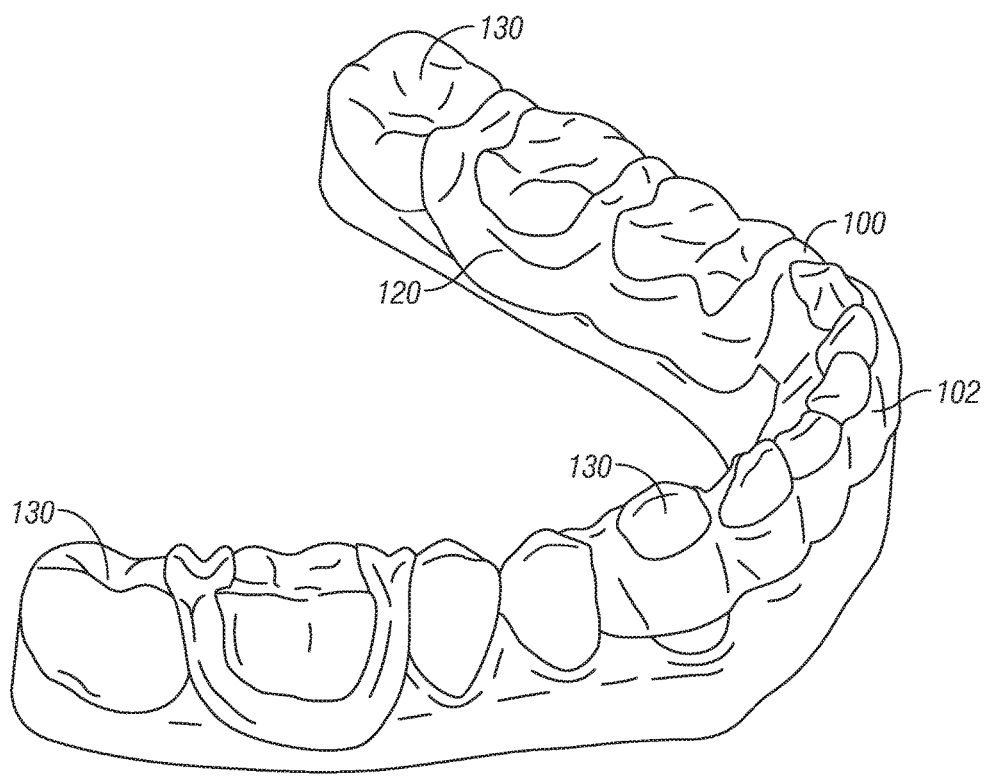

FIGS. 4A and 4B illustrate an example removable dental appliance 100 configured to reposition one or more teeth of a patient. Similarly, FIGS. 5A and 5B illustrate a 3D digital model of removable dental appliance 100 in combination with 3D digital model 130 of the dental structure of a patient.

Removable dental appliance 100 is configured to substantially expose occlusal surfaces of the teeth of a patient when worn by the patient. By providing exposed occlusal surfaces, removable dental appliance 100 may provide a number of advantages as compared to removable dental appliances that substantially surround the teeth of a patient such as, improved patient comfort, reduced visibility of the dental appliance, reduced tarter growth due to increase air and saliva flow between teeth, and the ability for a patient to eat or drink to some degree without removal of the dental appliance.

Removable dental appliance 100 includes appliance body 102. Appliance body 102 includes active band 112, which is configured to surround two or more teeth of the patient (in the depicted example, the anterior teeth). Active band 112 includes facial portion 106 and lingual portion 104. Facial portion 106 is configured to register with facial sides of the surrounded teeth within active band 112, whereas lingual portion 104 is configured to register with lingual sides of the surrounded teeth.

Facial portion 106 and lingual portion 104 cooperate to form receptacles 108. Each receptacle 108 represents a section of facial portion 106 and a corresponding section of lingual portion 104, the sections being configured to accept one of the surrounded teeth when dental appliance 100 is worn by the patient. Individual receptacles 108 may be separated by facial ridges 109 within facial portion 106 and lingual ridges 107 with lingual portion 104 of appliance body 102. Lingual ridges 107 and facial ridges 109 may correspond to interfaces between adjacent teeth of the surrounded teeth, but need not extend into interproximal areas of any two adjacent teeth.

Receptacles 108 at least partially define active band 112, which is formed by appliance body 102. Active band 112 is configured with an open end, such that occlusal surfaces of the surrounded teeth of the patient are exposed when removable dental appliance 100 is worn by the patient. For example, as worn by the patient, the surrounded teeth are positioned within individual receptacles 108 of appliance body 102. In the depicted examples, individual receptacles 108 are separated and/or individually defined by at least one of a lingual ridge and a facial ridge. In other examples, a receptacle may accept multiple adjacent teeth.

In order to facilitate positioning of the teeth of the patient, at least one of individual receptacles 108 may be misaligned as compared to the corresponding tooth of the patient. In this manner, appliance body 102 is configured to apply rotational and/or translational forces to the corresponding tooth of the patient when removable dental appliance 100 is worn by the patient. In the same or different examples, appliance body 102 is configured to apply translational forces to one or more of the teeth within individual receptacles 108. The active band 112 may also be configured to apply opposing forces on the both the labial and the lingual surfaces of the encircled teeth; this compressive "squeezing" can distinguish the operation of dental appliance 100 from other appliances including open-faced receptacles.

Removable dental appliance 100 further includes anchors 120. Anchors 120 extend from each side of appliance body 102. Each of anchors 120 includes a band 122 configured to accept a tooth of the patient and a strut 121 coupling the band 122 to the appliance body/active band 112. In the depicted example, the anchor band 122 encircles one or more posterior teeth of the patient. In some examples, the posterior tooth may be a premolar or a molar of the patient. When removable dental appliance 100 is worn by the patient with the surrounded teeth positioned within individual receptacles 108 of appliance body 102, the posterior teeth are positioned within bands 122 of anchors 120. Anchors 120 are configured such that occlusal surfaces of the accepted posterior teeth of the patient remain exposed when removable dental appliance 100 is worn by the patient. In other examples, the active band may be configured to surround one or more posterior teeth, with anchors located mesially or distally from the active band. Anchors, accordingly, may surround posterior teeth, anterior teeth, or a combination of both.

Removable dental appliance 100 may function as a spring aligner in that lingual portion 104 of appliance body 102 may be configured to apply force in a generally anterior direction to one or more of the surrounded teeth. Meanwhile, anchors 120 are configured to support the application of the force in the generally anterior direction by lingual portion 104 of appliance body 102 by applying forces in a generally posterior direction to the accepted posterior teeth when removable dental appliance 100 is worn by the patient. In alternative implementations (not shown), an appliance body may lack either a lingual portion or facial portion, such that one or more target teeth experience only one of an anterior or posterior directed force.

In some examples, removable dental appliance 100 may include a catch configured to connect to an orthodontic anchorage device within the mouth of the patient. Such a catch may be located on one or both of anchors 120.

In the same or different examples, removable dental appliance 100, including appliance body 102 and anchors 120, comprises one or more polymers. For example, removable dental appliance 100, including appliance body 102 and anchors 120, may consist of a single continuous 3D printed component. In some particular examples, the thickness of the components of removable dental appliance 100, including appliance body 102 and anchors 120 may be between about 0.25 millimeters and about 2.0 millimeters thick, such as between about 0.5 and about 1.0 millimeters thick, or about 0.75 millimeters thick. In some examples, thicknesses of features of removable dental appliance 100 may be varied to achieve more tailored forces. In the same or different examples, removable dental appliance 100 may include chamfers or fillets on edges of active band 112 and other spaces. Such chamfers or fillets may improve patient comfort and reduce the visibility of removable dental appliance 100.

In other examples, removable dental appliance 100 may include a metallic component configured to provide stiffness to a polymeric component to enhance forces applied by the removable dental appliance to one or more of the surrounded teeth. For example, the metallic component may comprise a wire extending between anchors 120 through lingual portion 104 of appliance body 102. In some examples, a removable dental appliance providing exposed occlusal surfaces when worn by a patient may include one or more other metal components, such as metal occlusal jumpers, where greater durability is needed to overcome the stress of high-pressure occlusal contact. The need for metal occlusal jumpers may be due to non-compliant patient activities, such as bruxing, or mastication. In the same or different examples, a removable dental appliance providing exposed occlusal surfaces when worn by a patient may include catches to connect to an anchorage device implanted within the patient. In this manner, such removable dental appliances providing exposed occlusal surfaces may provide a hybrid construction of metal and plastic.

While plastic components may be generally clear for reduced visibility, metal components may include plating or other coloring to reduce visibility of the removable dental appliance when worn by the patient. For example, metal components positioned near the teeth of a patient when implanted may include white coloring, whereas metal components positioned elsewhere may be colored to generally match tissue color within the mouth of the patient.

Removable dental appliance 100 may be digitally designed. In some examples, an ordered set of removable dental appliances is designed to be worn sequentially based on a series of digital setups. In such examples, each removable dental appliance in the set may be worn between about 2 weeks and about 12 weeks, such as between about 3 weeks and about 10 weeks or between about 4 weeks and about 8 weeks. After wearing removable dental appliance in the set for the prescribed time period, the removable dental appliance in the set may be discarded and replaced with the next removable dental appliance in the set. The design of removable dental appliance 100 may facilitate longer periods between changing of removable dental appliance within a set. For example, because active band 112 surrounds two or more teeth of the patient, lingual portion 104 and facial portion 106 may deflect to a greater degree when first worn by a patient than with similar dental appliance designs in which each tooth is isolated within a separate cavity. For this reason, removable dental appliance 100 may be designed to provide a greater amount of tooth movement than with similar dental appliance designs in which each tooth is isolated within a separate cavity, and can thereby be designed to be worn for a longer period of time by the patient before being replaced by the next dental appliance in the set.

While removable dental appliance 100 includes individual receptacles 108 within appliance body 102, in other examples, appliance body 102 may not include ridges that define separate cavities for each of the patient's teeth surrounded by appliance body 102. In addition while removable dental appliance 100 includes a single active band 112, other examples may include more than one active band, each active band surrounding one or more teeth. While not shown, removable dental appliance 100 and such other examples may optionally include one or more additional struts that connect, attach, or anchor the one or more active bands to each other, to the teeth, or to separate appliances that are bonded or otherwise attached directly to the teeth.

In this and other examples, the shapes and dimensions of active bands are defined such that a portion of each surrounded tooth surface is reproduced by the inner surface of removable dental appliance 100, including, for example, facial ridges 109 within facial portion 106 and lingual ridges 107 with lingual portion 104 of appliance body 102. Such reproduction may provide a conforming appliance in the relaxed state, which occurs at the end of appliance expression, while facilitating elastic deformation of removable dental appliance 100 in the stressed state, which is during the active period of appliance expression when the teeth are malposed relative to removable dental appliance 100.

By reproducing a somewhat significant portion of the labial and lingual surfaces of the teeth, but not so much of the occlusal surfaces, rotations of the teeth can be affected due to the formation of larger couples as the teeth are more malposed relative to removable dental appliance 100. By closely reproducing the features of the teeth in the inner surfaces of removable dental appliance 100, removable dental appliance 100 may be especially effective at finishing cases due to the existence of couples when removable dental appliance 100 is deformed even slightly. In contrast, many existing removable appliances, such as spring aligners or Inman aligners, avoid the reproduction of detail in these surfaces to avoid interference with the teeth as they move, so that the teeth can be moved over greater distances or angles using a single appliance. The removal of detail in these appliances serves to provide a smooth surface over which the teeth may glide as they move, but the disadvantage is that the couples formed by contact points that cause intended rotations are much smaller in magnitude, which leads to smaller forces and less appliance expression.

To use an analogy, an open-ended wrench is more effective when the inner surfaces of the jaws are designed to closely conform to a corresponding nut (i.e., straight and parallel). But, if the inner surfaces of the jaws are rounded so that the distance between the jaws is at a minimum at the middle point and increasing toward the opening at either end, a couple formed by the contact points between the jaws and the nut while torqueing the wrench will have a smaller radius than it otherwise would if the jaws were parallel and contacted the nut at its vertices (assuming some tolerance between the jaws and the nut). Similarly, an increase in the width (i.e., occlusal gingival thickness) of the active band 112 of removable dental appliance 100 will result in an increase in the radius of the couple, which will increase the applied force during appliance deformation. Although, in some cases, the motivation may be to minimize the width of the bands for reasons of aesthetics or patient comfort (e.g., all the way down to a thin wire), in other cases, it may be advantageous to trade perceived aesthetics for greater function by increasing the inner surface area of removable dental appliance 100 and closely reproducing the features of the teeth.

Removable dental appliance 100 may be manufactured using an automated manufacturing system, such as automated manufacturing system 74 (FIG. 3), based on a digital model of removable dental appliance 100 produced by a computer system, such as computer 70 (FIG. 3). In different examples, removable dental appliance 100 may be formed using 3D printing or thermo-formed and trimmed, such as trimmed with 5-axis milling or laser cutting. With 3D printing, removable dental appliance 100 may be 3D printed directly by a 3D printing system, but in other examples, removable dental appliance 100 may be thermoformed over a mold of teeth formed using 3D printing. In some examples, the 3D printed teeth may have raised occlusal surfaces, or are otherwise different from patient's teeth, to limit the need for removing material from occlusal surface areas after thermoforming removable dental appliance 100 over the mold of teeth formed using 3D printing.

In the same or different examples, automated or semi-automated manufacturing of removable dental appliance 100 may include injection molding, lost wax casting, 5-axis milling, laser cutting and other manufacturing techniques. In examples where a removable dental appliance includes one or more metal components, such as metal occlusal jumpers, automated manufacturing may include robotic manipulation of metallic components, such robotic bending of metallic components like wires. Removable dental appliances providing a hybrid construction of metal and plastic may also be manufactured using overmolding and/or snap-fit techniques. Such metal components may also be digitally designed and fabricated from metal wires, custom-bent by a robot, from metal investment castings of 3D-printed wax models, from "direct metal" 3D printing, including, Selective Laser Melting (SLM) or Selective Laser Sintering (SLS), or from 3-, 4-, or 5-axis milling of metal blocks. Alternately, stronger components for use in combination with polymer components of a removable dental appliance could be fabricated from clear or tooth-colored ceramic materials. In some examples, metal may be plated with a "white" jewelry metal, such as silver, platinum, palladium, or rhodium, in order to improve aesthetics. In general, adding more components would introduce joints, and some assembly may be required following an automated or semi-automated manufacturing process.

In this manner, the techniques disclosed herein with respect to removable dental appliances that provide exposed occlusal surfaces facilitate many varied configurations. The techniques facilitate selecting both treated teeth and anchoring teeth, as well as selecting customized sizes, shapes, and placement of force members, anchors, and other features. In addition, material combinations and joint types may also be selected to provide a desired therapy outcome for a patient.

Figure 6:
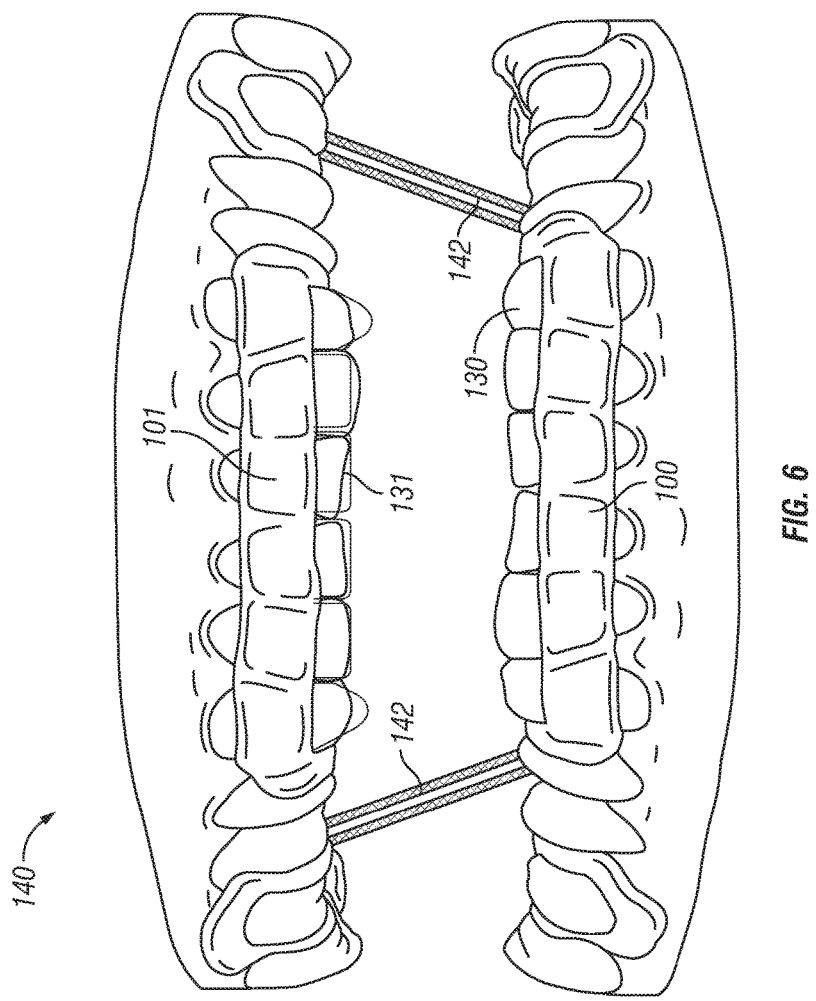
FIG. 6 illustrates a 3D digital model of upper and lower removable dental appliances that facilitate correction of a Class II malocclusion.

FIG. 6 illustrates 3D digital model 140 of upper removable dental appliance 101 and lower removable dental appliance 100 that facilitate correction of a class II malocclusion. FIG. 6 further illustrates 3D digital model 130 of the lower teeth of a patient and 3D digital model 131 of the upper teeth of the patient. Lower removable dental appliance 100 is similar to removable dental appliance 100 as illustrated in FIGS. 4A-5B but with the addition of knobs, hooks, loops, catches, or other features to connect to elastic ligatures 142. In addition, upper removable dental appliance 101 is similar to removable dental appliance 100, except that it is configured to be worn over the upper teeth of the patient shown in 3D digital model 131. Upper removable dental appliance 101 also includes hooks or other features to connect to elastic ligatures 142. In other examples, an appliance may use a FORSUS Class II corrector or Herbst corrector to connect upper and lower arches via a sliding "shock absorber." In the case of a FORSUS connector, a coiled spring is compressed when the mandible closes. When the mandible opens, the spring relaxes and slides freely once it reaches the end of its range. FORSUS or Herbst Class II correctors only push on the dental appliance, not pull, and may be more suitable for inclusion within a removable appliance than elastic ligatures 142, which might tend to pull upper removable dental appliance 101 and lower removable dental appliance 100 off of the patient's teeth.

Like removable dental appliance 100, removable dental appliance 101 is configured to expose occlusal surfaces of the teeth of a patient when worn by the patient. Like removable dental appliance 100, removable dental appliance 101 may function as a spring aligner in that it may be configured to apply force in a generally anterior direction to one or more of the surrounded teeth. Removable dental appliance 101 also includes anchors to support the application of force in the generally anterior direction when removable dental appliance 101 is worn by the patient, although the anchors may also support the application of force in a generally distal direction in other examples. The generally anterior direction may vary among the teeth of the patient as forces applied by removable dental appliance 101 tend to squeeze the teeth together, such that the force experienced by one or more teeth may vary from the generally anterior direction. In general, the loop formed by removable dental appliance 101 expanded by the malposed teeth, and removable dental appliance 101 forces the teeth into various translations and rotations as it attempts to relax into its equilibrium state, which has a smaller perimeter. Upper removable dental appliance 101 may be manufactured using techniques as described with respect to FIGS. 4A-5B and removable dental appliance 100.

Upper removable dental appliance 101 is configured to interact with lower removable dental appliance 100 such that the combination of upper removable dental appliance 101 and lower removable dental appliance 100 facilitates correction of class II malocclusion. In particular, upper removable dental appliance 101 includes hooks or other features to connect to elastic ligatures 142. Lower removable dental appliance 100 also includes hooks or other features to connect to elastic ligatures 142. Elastic ligatures 142 provide correction of a class II malocclusion when worn by a patient in combination with upper removable dental appliance 101 and lower removable dental appliance 100. To prevent elastic ligatures 142 from pulling upper removable dental appliance 101 and lower removable dental appliance 100 off the teeth one or both of upper removable dental appliance 101 and lower removable dental appliance 100 may engage bonded attachments on the teeth. Exemplary bonded attachments may be found in U.S. Pat. No. 8,827,697 to Cinader et al., titled, "LINGUAL ORTHODONTIC APPLIANCE WITH REMOVABLE SECTION," and issued on Sep. 9, 2014. U.S. Pat. No. 8,827,697 is herein incorporated by reference in its entirety.

Figure 7:
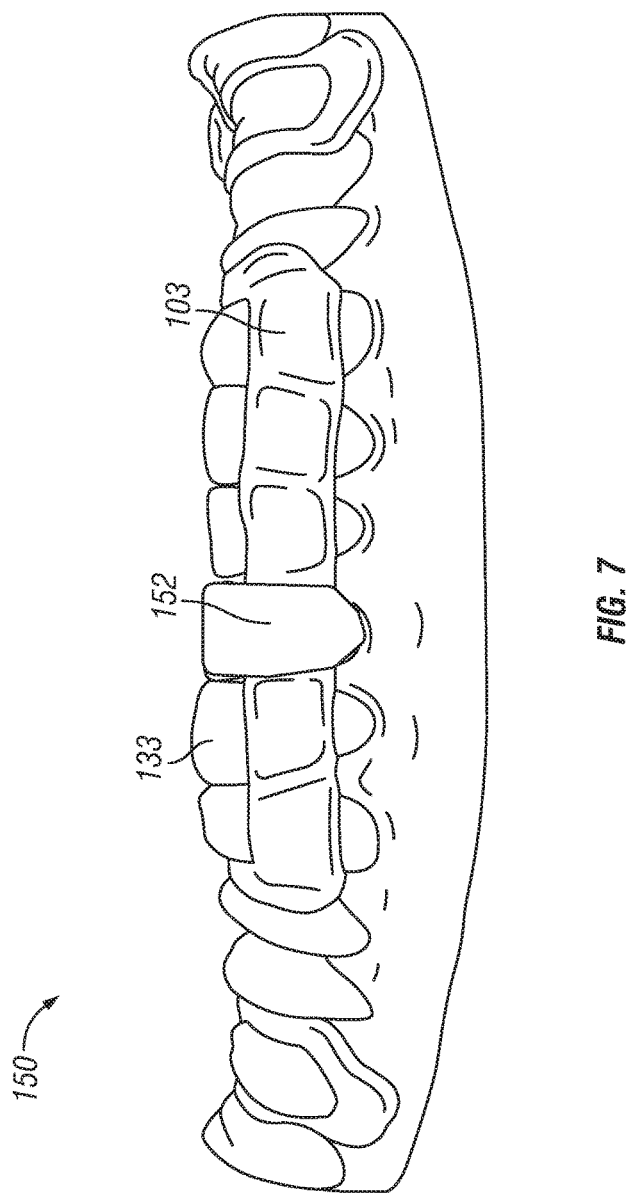
FIG. 7 illustrates the anterior portion of a 3D digital model of a removable dental appliance including a pontic in combination with a 3D digital model of the teeth of a patient.

FIG. 7 illustrates the anterior portion of 3D digital model of removable dental appliance 150, with active band 103 and including pontic 152 in combination with 3D digital model 133 of the teeth of a patient. Removable dental appliance 150 is the same or similar to removable dental appliance 100 as illustrated in FIGS. 4A-5B but with the addition of pontic 152.

Like removable dental appliance 100, removable dental appliance 150 is configured to expose occlusal surfaces of the teeth of a patient when worn by the patient. Like removable dental appliance 100, removable dental appliance 150 may function as a spring aligner in it may be configured to apply force in a generally anterior direction to one or more of the surrounded teeth. The generally anterior direction may vary among the teeth of the patient as forces applied by removable dental appliance 100 tend to squeeze the teeth together, such that the force experienced by one or more teeth may vary from the generally anterior direction. In general, the loop formed by removable dental appliance 100 expanded by the malposed teeth, and removable dental appliance 100 forces the teeth into various translations and rotations as it attempts to relax into its equilibrium state, which has a smaller perimeter. Removable dental appliance 150 also includes anchors to support the application of the force in the generally anterior direction when removable dental appliance 150 is worn by the patient. Removable dental appliance 150 may be manufactured using techniques as described with respect to FIGS. 4A-5B and removable dental appliance 100.

Pontic 152 is configured to fill a space from a missing tooth of the patient, as represented in 3D digital model 133 of the teeth of the patient. In some examples, pontic 152 may be colored for consistency with the teeth of the patient. The geometry of pontic 152 may be selected in order to aid in the repositioning of teeth adjacent to pontic 152. For example, in an ordered set of removable dental appliances, each including a pontic, the pontic may become progressively larger throughout the sequence of the ordered set of removable dental appliances in order to create sufficient space for a desired implant, bridge or other cosmetic tooth.

Figure 8:
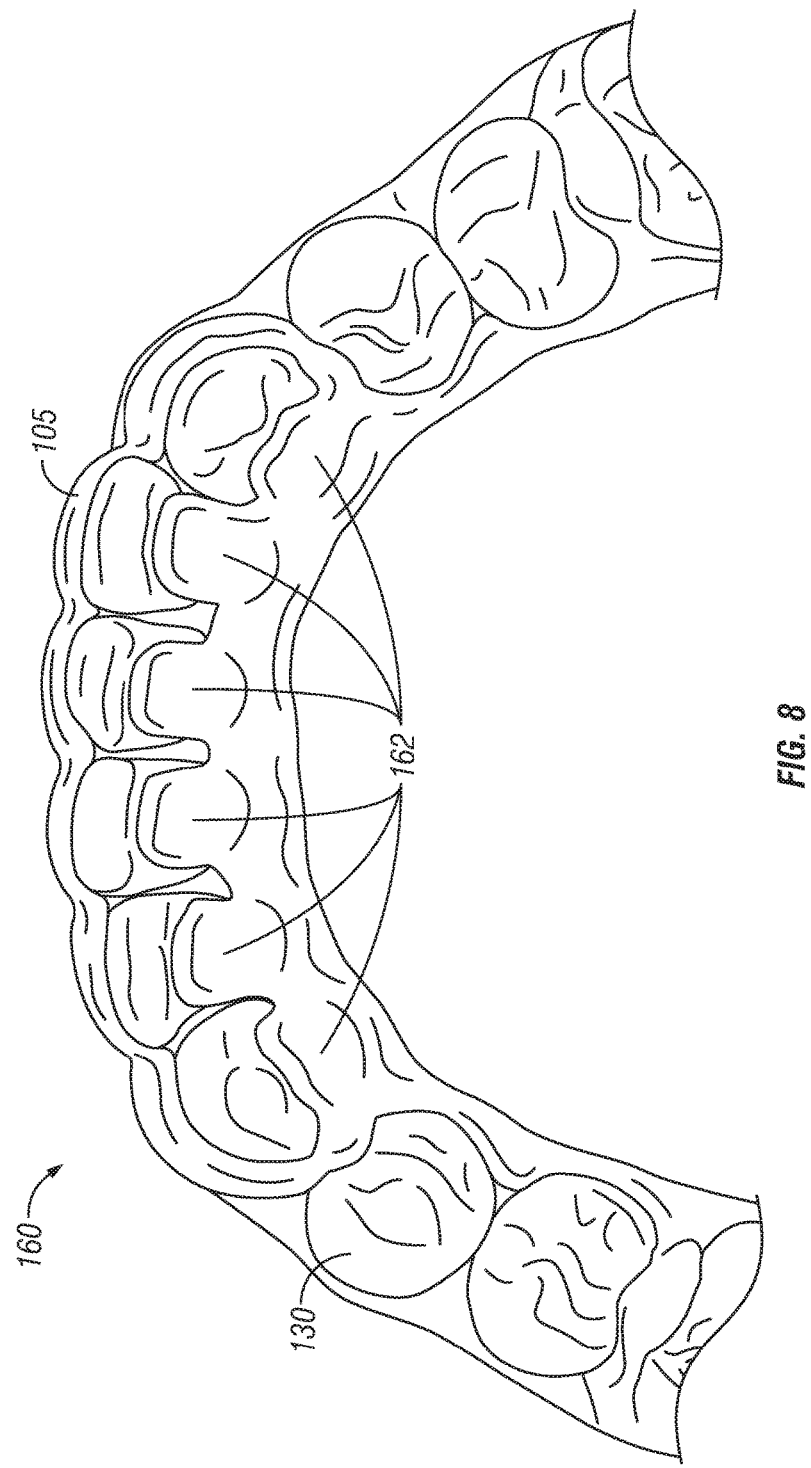
FIG. 8 illustrates the anterior portion of a 3D digital model of a removable dental appliance including lingual fingers and providing exposed occlusal surfaces in combination with a 3D digital model of the teeth of a patient.

FIG. 8 illustrates the anterior portion of 3D digital model of a removable dental appliance 160, with active band 105 and including lingual fingers 162 and providing exposed occlusal surfaces in combination with 3D digital model 130 of the teeth of a patient. Removable dental appliance 160 is the same or similar to removable dental appliance 100 as illustrated in FIGS. 4A-5B with the addition of lingual fingers 162.

Like removable dental appliance 100, removable dental appliance 160 is configured to expose occlusal surfaces of the teeth of a patient when worn by the patient. Like removable dental appliance 100, removable dental appliance 160 may function as a spring aligner in that it may be configured to apply force in a generally anterior direction to one or more of the surrounded teeth. Removable dental appliance 160 also includes anchors to support the application of the force in the generally anterior direction when removable dental appliance 160 is worn by the patient.

Lingual fingers 162 may apply separate forces generally in the anterior direction to each of the surrounded teeth. The direction and magnitude applied to each of the surrounded teeth may be customized according to the design of the adjacent one of lingual fingers 162. In different examples, lingual fingers 162 may be between about 0.25 millimeters and about 2.0 millimeters thick, such as between about 0.5 and about 1.0 millimeters thick, or about 0.75 millimeters thick. Removable dental appliance 160 may be manufactured using techniques as described with respect to FIGS. 4A-5B and removable dental appliance 100.

When removable dental appliance 160 is worn by the patient, lingual fingers 162, if located on the lingual portion of the dental appliance, apply forces generally in the anterior direction by pushing the teeth forward against the labial bow (anterior portion of the dental appliance). However, a labial bow of removable dental appliance 160 also pushes back on the teeth in a lingual direction. The double action of teeth being pushed simultaneously from opposite sides and opposite directions causes couples to be formed at the opposing contact points. Where these couples form relative to the center of moments determines the axis of rotation and the magnitude of the leverage achieved. If contact is made only from one side, and no couple is formed, then the tooth is translated. However, because the contact point is on the crown of the tooth, and the center of moments is somewhere in the middle of the root, pure translation is not achieved and instead manifests as rotation about a long arm, the distance from the contact point to the center of moments in the root. This only approximates rotation. Pure translation may be achieved by firmly embracing the tooth locally and having other, more distant parts of the dental appliance undergo deformation which results in a translational force. As such, it may be advantageous to embrace certain teeth individually, not as a group, and use struts between these teeth and other, anchoring teeth as the elastically deformed force members. In this way, removable dental appliance 160 may be used to create space between the anterior and posterior segments by pushing all of the anterior teeth forward, as a group, against the posterior teeth, which serves as anchors (but which may also move in an opposite direction themselves).

Figure 9:
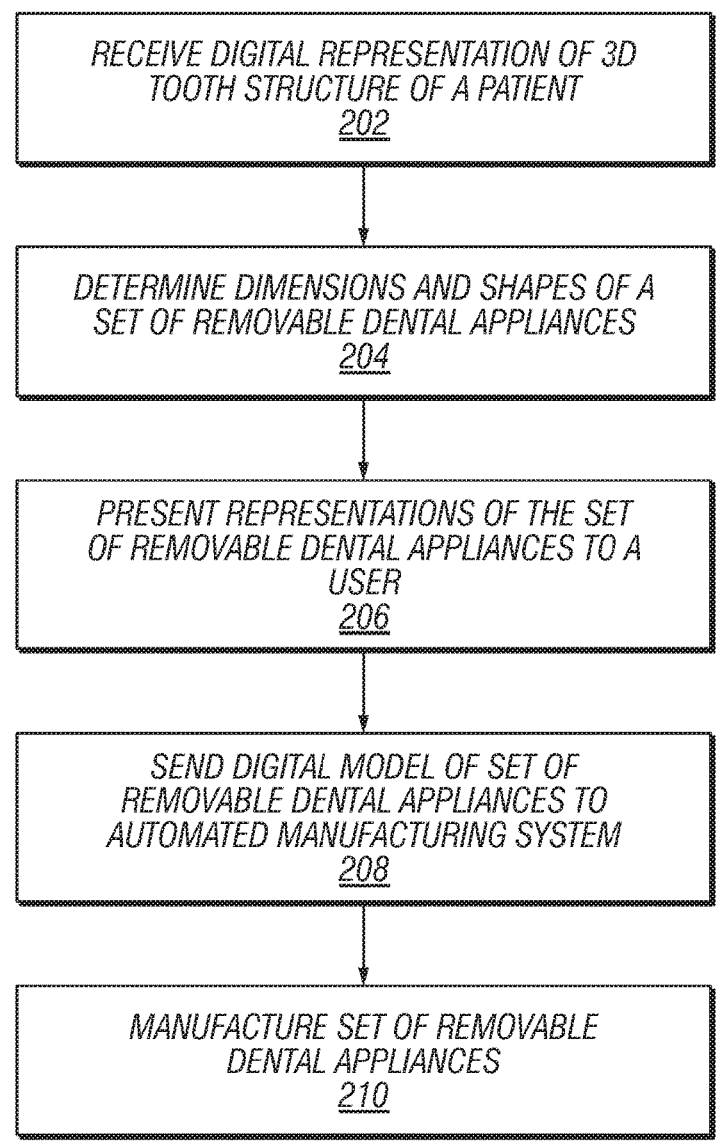
FIG. 9 is a flow diagram illustrating a process conducted at a manufacturing facility for construction of a set of removable dental appliances.

FIG. 9 is a flow diagram illustrating process 100 conducted at manufacturing facility 48 for construction of removable dental appliances 52 (FIG. 1). In some examples, removable dental appliances 52 may include one or more of removable dental appliance 100, removable dental appliance 101, removable dental appliance 150 and/or removable dental appliance 160. Computer 70 at manufacturing facility 48 receives digital tooth structure data 46, patient providing initial positions of one or more teeth of the patient, and prescription data 47 (202) from clinic 44. Alternatively, computer 70 retrieves the information from a database located within or otherwise accessible by computer 70. A trained user associated with computer 70 may interact with a computerized modeling environment running on computer 70 to develop a treatment plan relative to the digital representation of the patient's tooth structure and generate prescription data 47, if clinic 44 has not already done so. In other examples, computer 70 may automatically develop a treatment plan based solely on the patient's tooth structure and predefined design constraints.

Once computer 70 receives patient's tooth structure, computer 70 determines dimensions and shapes of a removable dental appliance for the patient (204). The dimensions and shapes of the removable dental appliance are configured to reposition the one or more teeth of the patient from their initial positions to adjusted positions when the removable dental appliance is worn by the patient. In the same or additional examples, computer 70 determines dimensions and shapes of a set of removable dental appliances for the patient, the set of removable dental appliances for the patient being configured to be worn in series.

In some examples, determining dimensions and shapes of the removable dental appliance includes selecting, with computer 70, the dimensions and shapes of the removable dental appliance according to a set of predefined design constraints. The set of predesigned design constraints may include one or more factors, including, but not limited to, a maximum localized force applied to one or more of the surrounded teeth, a maximum rotational force applied to one or more of the surrounded teeth, a maximum translational force applied to one or more of the surrounded teeth, a maximum total force applied to one or more of the surrounded teeth, and a maximum strain applied to the removable dental appliance when worn by the patient when the surrounded teeth are in their initial positions.

Computer 70 may use finite element analysis (FEA) techniques to analyze forces on a patient's teeth as well as the removable dental appliance during the determination of the dimensions and shapes of the removable dental appliance. For example, computer 70 may apply FEA to a solid model of the patient's teeth as the modeled teeth move from their initial positions to their final positions representing a treatment including an ordered set of removable dental appliances. Computer 70 may use FEA select appropriate of the removable dental appliance to apply the desired forces on the teeth. In addition, computer 70 may use a virtual articulator may to determine contact points between the teeth throughout the movement of the modeled teeth during the treatment. Computer 70 may further include occlusal contact forces, such as interdigitation forces, in the FEA forces analysis in combination with forces from device during the design of removable dental appliances in an ordered set of removable dental appliances.

In the same or different examples, determining dimensions and shapes of the removable dental appliance includes selecting, with computer 70 thicknesses of the facial portion and the lingual portion of the dental appliance body in order to provide a stiffness suitable to reposition the one or more teeth of the patient from their initial positions to adjusted positions when the removable dental appliance is worn by the patient. In different examples, such selected thickness may range between about 0.25 millimeters and about 2.0 millimeters thick, such as between about 0.5 and about 1.0 millimeters thick. In some examples, computer 70 may further select a material of at least a portion of the removable dental appliance (e.g., the facial and lingual body portions) according to the predefined design constraints or to provide a desired stiffness characteristic without necessarily increasing the thickness.

The dimensions and shapes of a removable dental appliance for the patient may be presented to a user via user interface of 72 of computer 70 (206). In examples in which dimensions and shapes of the removable dental appliance are presented to a user via user interface of 72 of computer 70, the user may have the opportunity to adjust the design constraints or directly adjust the dimensions and shapes of the removable dental appliance before the design data is sent to automated manufacturing system.

Alternatively or additionally, the dimensions and shapes of a removable dental appliance for the patient may be presented to a user by computer 70 directly as the removable dental appliance manufactured by automated manufacturing system 74 (206). In such examples, computer 70 sends a digital model of the removable dental appliance to automated manufacturing system 74, and automated manufacturing system 74 manufactures the removable dental appliance according to the digital model from computer 70.

However, even in examples where the dimensions and shapes of a removable dental appliance for the patient may be presented to a user via user interface of 72 of computer 70, following user approval, computer 70 sends a digital model of the removable dental appliance to automated manufacturing system 74 (208), and automated manufacturing system 74 manufactures the removable dental appliance according to the digital model from computer 70 (210).

In some examples, automated manufacturing system 74 may include a 3D printer. Forming shapes of the active bands of the dental appliance body may include printing the surfaces of the dental appliance body that form the active bands of the dental appliance body with the 3D printer. Such active bands have been described previously with respect to removable dental appliance 100. In other examples, forming shapes of the active bands of the dental appliance body may include printing representations of the teeth of the patient with the 3D printer and thermoforming the dental appliance body over the representations of the teeth of the patient. For example, the representations of the teeth of the patient may include raised occlusal surfaces to facilitate forming the space that separates the facial portion from the lingual portion in the thermoformed appliance body.

The techniques of FIG. 9 may be applied to design and manufacture of each of an ordered set of removable dental appliances for the patient. For example, each removable dental appliance in the ordered set of removable dental appliances may be configured to incrementally reposition the teeth of the patient. In this manner, the ordered set of removable dental appliances may be configured to reposition the teeth of the patient to a greater degree than any one of the removable dental appliances within the set of the removable dental appliances. Such an ordered set of removable dental appliances for the patient may specifically be configured to incrementally reposition the one or more teeth of the patient from their initial positions to final adjusted positions as the removable dental appliances of the ordered set of removable dental appliances for the patient are worn sequentially by the patient.

In some examples, the techniques described with respect to FIG. 9 may be embodied within a computer-readable storage medium, such as a computer-readable storage medium of client computing device 80 (FIG. 3) and or computer 70 (FIG. 3). The computer-readable storage medium storing computer-executable instructions that, when executed, configure a processor to perform the techniques described with respect to FIG. 9.

Following the design of removable dental appliances 52, manufacturing facility 48 fabricates removable dental appliances 52 in accordance with the digital tooth structure data 46 and prescription data 47 (206). Construction of removable dental appliances 52 may include 3D printing, thermoforming, injection molding, lost wax casting, 5-axis milling, laser cutting, hybrid plastic and metal manufacturing techniques, such as snap-fitting and overmolding, as well as other manufacturing techniques.

Figure 10:
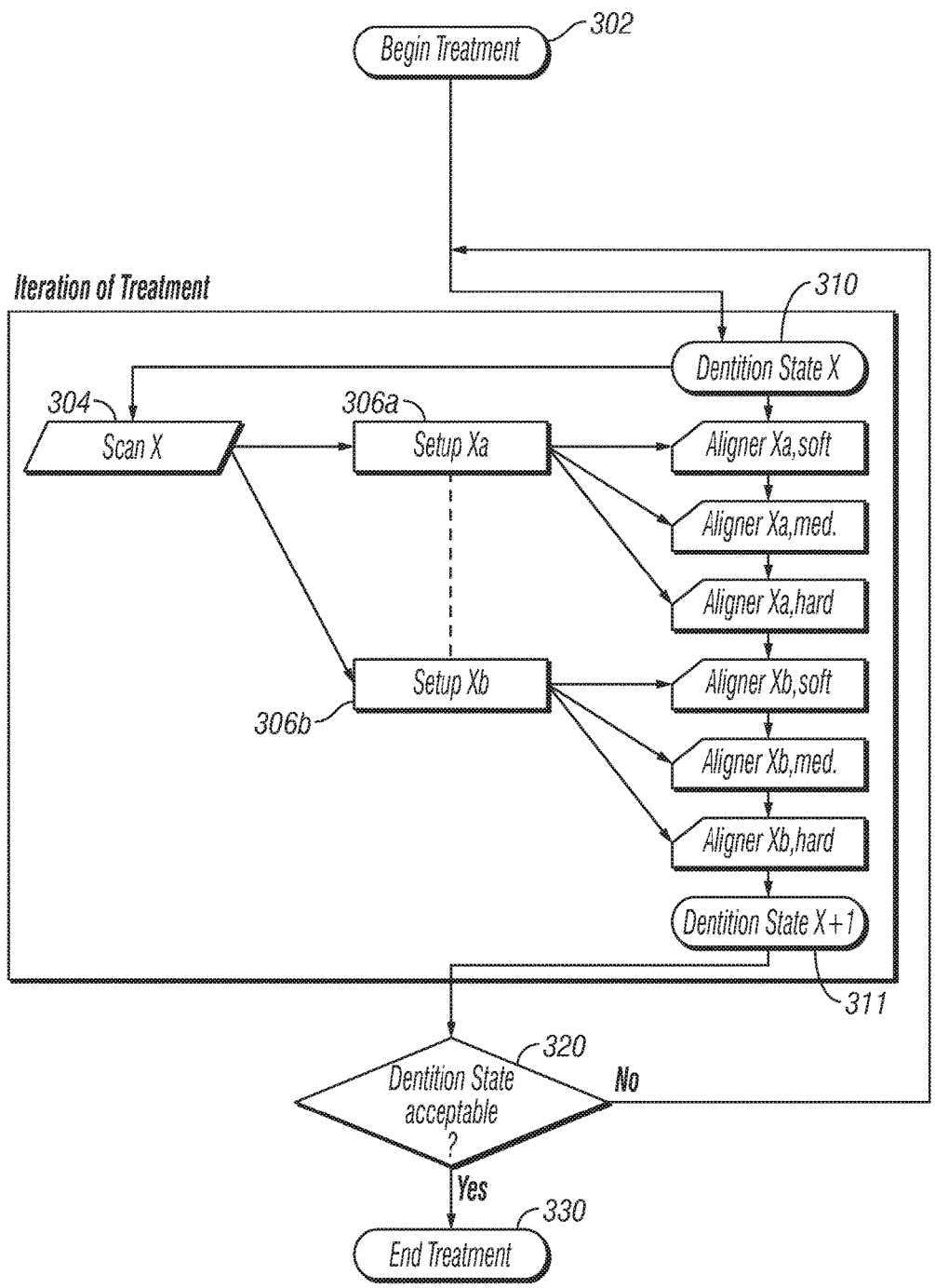
FIG. 10 is a flow diagram illustrating successive iterations of treatment using an ordered set of removable dental appliances.

FIG. 10 is a flow diagram illustrating successive iterations of treatment using an ordered set of removable dental appliances. The ordered set of removable dental appliances is configured to reposition one or more teeth of a patient. In various examples, the ordered set of removable dental appliances may include one or more of removable dental appliance 100, removable dental appliance 101, removable dental appliance 150, removable dental appliance 160, and/or any of the other removable dental appliances described further below. Accordingly, treatment may feature a plurality of the removable dental appliances described herein and need not be limited to iterations of one particular dental appliance embodiment. In one exemplary implementation, the treatment may initially begin with iterations of one or more removable dental appliance 800 (see FIGS. 15A and 15B below) and, once the patient's teeth have moved a certain desired amount, treatment may continue with iterations of removable dental appliance 100.

Treatment begins with the first iteration of treatment (302). At the beginning of the first iteration of treatment, the patient's teeth are at their initial positions as represented by detention state X (310). A scan of the patient's teeth are taken to facilitate the design of the ordered set of removable dental appliances (304). From the scan of patient's teeth, a computer determines two different shape and dimensions for removable dental appliances in the ordered set: design 306a and design 306b. Example techniques for creating a digital model of a patient's teeth are described in U.S. Pat. No. 8,738,165 to Cinader et al., titled, "METHODS OF PREPARING A VIRTUAL DENTITION MODEL AND FABRICATING A DENTAL RETAINER THEREFROM," and issued on May 27, 2014. U.S. Pat. No. 8,738,165 is herein incorporated by reference in its entirety. The computer may determine two different shape and dimensions for removable dental appliances in the ordered set by first adjusting the digital model of the patient's teeth to create a model of the desired position of the patient's teeth following the therapy. Then, the computer may create the shape and dimensions for removable dental appliances in the ordered set based on the time and forces required to move the patient's teeth from the initial positions to their desired positions. For example, the computer model may adjust the thicknesses and other dimensions of spring-like elements of the removable dental appliances in the ordered set to produce the forces required to move the patient's teeth from the initial positions to their desired positions. The modeled forces applied by removable dental appliances in the ordered set may further be based on the incremental positional movements of the patient's teeth during the treatment. In this manner, the computer may design shape and dimensions for each of the removable dental appliances in the ordered set according to expected forces applied on the teeth for in there predicted positions at the time during the treatment the removable dental appliances in the ordered set is to be worn by the patient.

In some examples, more than one, such as three, different removable dental appliances in the set of removable dental appliances can be manufactured using each of the two different shape and dimensions to produce six removable dental appliances in the set of removable dental appliances. The first through third dental appliances within the ordered set of dental appliances are of the same shape and dimensions, but comprise materials with different stiffness characteristics. The second and third dental appliances have higher stiffness characteristics than first dental appliance and the third dental appliance also having higher stiffness characteristics than second dental appliance. Likewise, the fourth through sixth dental appliances within the ordered set of dental appliances are of the same shape and dimensions, but comprise materials with different stiffness characteristics. The fifth and sixth dental appliances having higher stiffness characteristics than fourth dental appliance and the sixth dental appliance also having higher stiffness characteristics than fifth dental appliance. In some examples, the first dental appliance may have the same stiffness characteristics as the fourth dental appliance. Likewise, in some examples, the second dental appliance may have the same stiffness characteristics as the fifth dental appliance. Further, in some examples, the third dental appliance may have the same stiffness characteristics as the sixth dental appliance.

In one exemplary treatment methodology, the first removable dental appliance in the ordered set of removable dental appliances is made from a relatively soft material, such as a relatively soft polymeric material. The first removable dental appliance in the ordered set of removable dental appliances conforms to design 306a, and is made from a relatively soft material, such as a relatively soft polymeric material. The second removable dental appliance in the ordered set of removable dental appliances conforms to design 306a, and is made from a material of medium stiffness, such as a relatively stiffer polymeric material than with the first removable dental appliance in the ordered set of removable dental appliances. The third removable dental appliance in the ordered set of removable dental appliances conforms to design 306a, and is made from a material of high stiffness, such as a relatively stiffer polymeric material than with the second removable dental appliance in the ordered set of removable dental appliances. The fourth removable dental appliance in the ordered set of removable dental appliances conforms to design 306b, and is made from the relatively soft material. The fifth removable dental appliance in the ordered set of removable dental appliances conforms to design 306b, and is made from a material of medium stiffness. The sixth removable dental appliance in the ordered set of removable dental appliances conforms to design 306b, and is made from the material of high stiffness.

The first through sixth removable dental appliances in the ordered set of removable dental appliances are worn in sequence over time by the patient. For example, each of the removable dental appliances in the ordered set of removable dental appliances may be worn between about 2 weeks and about 12 weeks, such as between about 3 weeks and about 10 weeks or between about 4 weeks and about 8 weeks. Following the treatment plan using the first through sixth removable dental appliances the patient's teeth are at their final positions for the first iteration of treatment as represented by detention state X+1 (311).

At this point, the patient may return to the clinician who may evaluate the result of the first iteration of treatment (320). In the event that the first iteration of treatment has resulted in satisfactory final placement of the patient's teeth, the treatment may be ended (330). However, if the first iteration of treatment did not complete the desired movement of the patient's teeth, one or more additional iterations of treatment may be performed. To begin the next iteration of treatment, the clinician may taking another scan of the patient's teeth are taken to facilitate the design of the ordered set of removable dental appliances (304). In some examples, evaluation of the result of the first iteration of treatment may include taking another scan of the patient's teeth, in which case beginning the next iteration of treatment may simply involve forwarding the digital model of the patients teeth to a manufacturing facility so that another ordered set of removable dental appliances may be manufactured for the patient based on the new positions of the patient's teeth. In yet other examples, the newly acquired scan may be used to create one or more iterations of removable dental appliances in the clinician's facility.

The techniques of FIG. 10 represent one specific example, and a variety of modifications may be made to the techniques of FIG. 10 within the spirit of this disclosure. For example, an ordered set of removable dental appliances may include more or less than six removable dental appliances. As another example, each removable dental appliance in the ordered set of removable dental appliances may have unique shapes and dimensions. As another example, the computer determines a single shape and dimension for removable dental appliance(s) in the ordered set from the initial scan X of the patient's teeth.

Figure 11A:
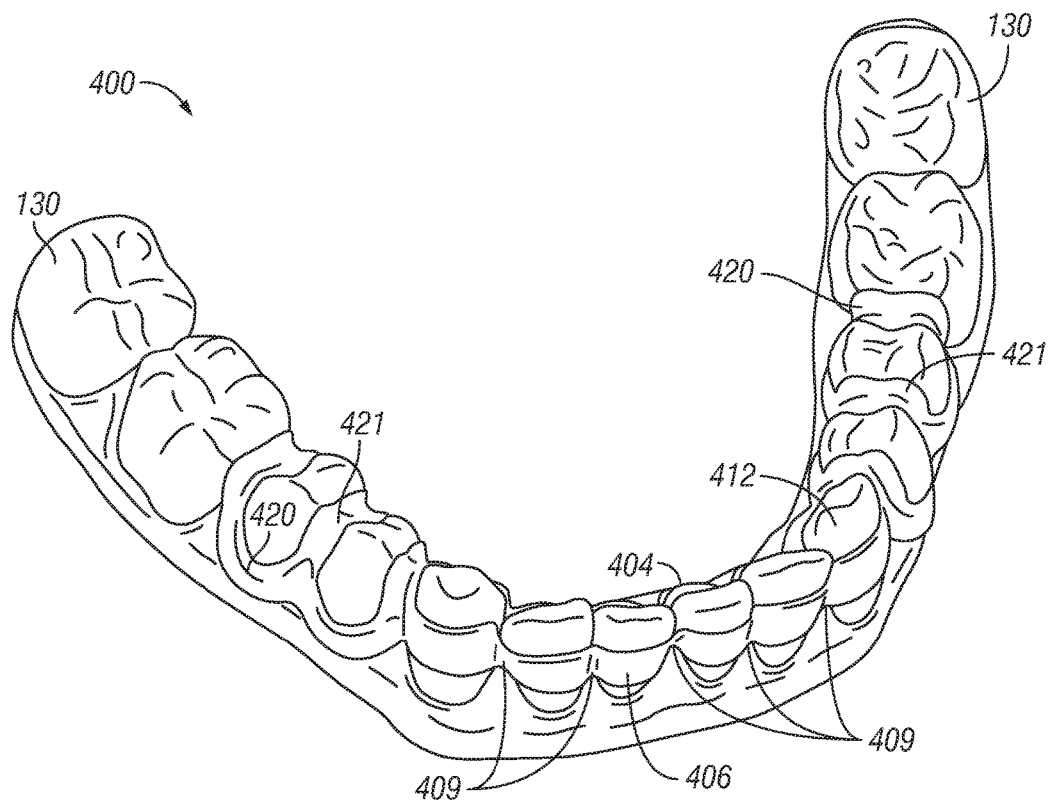
FIGS. 11A and 11B illustrate an example removable dental appliance providing exposed occlusal surfaces when worn by a patient, the example removable dental appliance relying on two adjacent posterior teeth in each quadrant of the mouth for anchorage by surrounding the teeth.
Figure 11B:
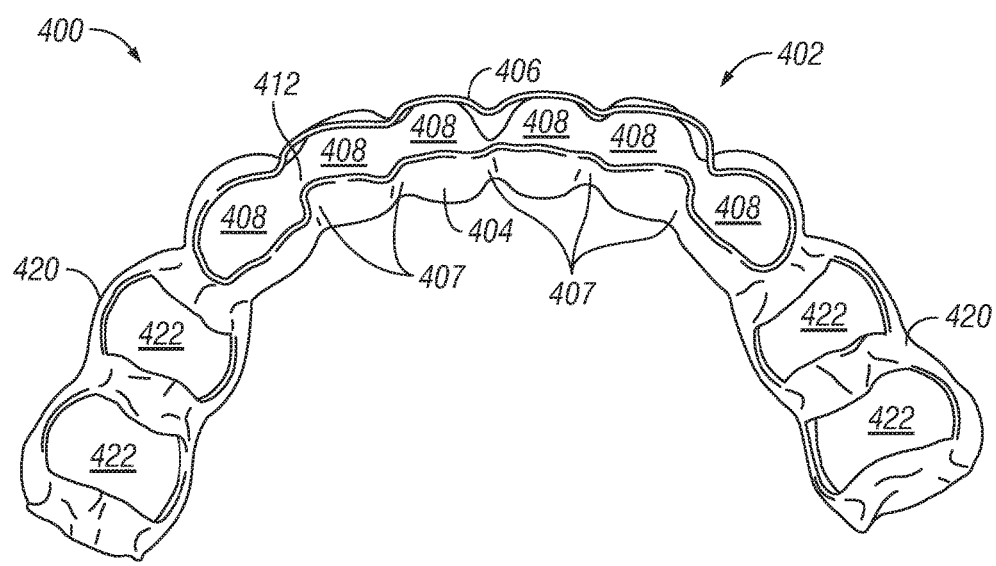

FIGS. 11A and 11B illustrate an example removable dental appliance providing exposed occlusal surfaces when worn by a patient, the example removable dental appliance including anchors configured to accept two posterior teeth of the patient on each side. FIG. 11A further illustrates a 3D digital model of removable dental appliance 400 in combination with 3D digital model 130 of the teeth of a patient. Removable dental appliance 400 may be substantially similar to removable dental appliance 100 (FIG. 4A-5B) with the exception of the configuration of anchors 420. For brevity, details of removable dental appliance 400 that are the same or similar to details previously described with respect to removable dental appliance 100 are described in limited or no detail with respect to removable dental appliance 400.

Removable dental appliance 400 is configured to expose occlusal surfaces of the teeth of a patient when worn by the patient. Removable dental appliance 400 includes appliance body 402. Appliance body 402 forms active band 412, which is configured to surround two or more teeth of the patient. Appliance body 402 includes facial portion 406 and lingual portion 404. Facial portion 406 is configured to register with facial sides of the surrounded teeth, whereas lingual portion 404 is configured to register with lingual sides of the surrounded teeth.

Facial portion 406 and lingual portion 404 form receptacles 408. Each receptacle 408 represents a section of facial portion 406 and a corresponding section of lingual portion 404 configured to accept one of the surrounded teeth when dental appliance 400 is worn by the patient. Receptacles 408 may be separated by facial ridges 409 within facial portion 406 and lingual ridges 407 with lingual portion 404 of appliance body 402. Lingual ridges 407 and facial ridges 409 may correspond to interfaces between adjacent teeth of the surrounded teeth.

Active band 412 is configured such that occlusal surfaces of the surrounded teeth of the patient are exposed when removable dental appliance 400 is worn by the patient. For example, as worn by the patient, the surrounded teeth are positioned within receptacles 408 of appliance body 402.

In order to facilitate positioning of the teeth of the patient, at least one of receptacles 408 may be misaligned as compared to the corresponding tooth of the patient. In this manner, appliance body 402 may be configured to apply rotational and/or translational forces to the corresponding tooth of the patient when removable dental appliance 400 is worn by the patient. In some particular examples, appliance body 402 may be configured to provide only compressive or liner forces. In the same or different examples, appliance body 402 may be configured to apply translational forces to one or more of the teeth within receptacles 408.

Removable dental appliance 400 further includes anchors 420. Anchors 420 extend from each side of appliance body 402. Each of anchors 420 includes two receptacles 422 configured to accept a posterior tooth of the patient. Receptacles 422 are separated from active band 412 by interdental braces 421. In some examples, the posterior teeth may include a premolar and/or a molar of the patient. When removable dental appliance 400 is worn by the patient with the surrounded teeth positioned within receptacles 408 of appliance body 402, the posterior teeth are positioned within receptacles 422 of anchors 420. Anchors 420 are configured such that occlusal surfaces of the accepted posterior teeth of the patient remain exposed when removable dental appliance 400 is seated on the patient's dental arch.

Removable dental appliance 400 may function as a spring aligner in that lingual portion 404 of appliance body 402 may be configured to apply force in a generally anterior direction to one or more of the surrounded teeth. Meanwhile, anchors 420 are configured to support the application of the force in the generally anterior direction by lingual portion 404 of appliance body 402 by applying forces in a generally posterior direction to the accepted posterior teeth when removable dental appliance 400 is worn by the patient.

Figure 12:
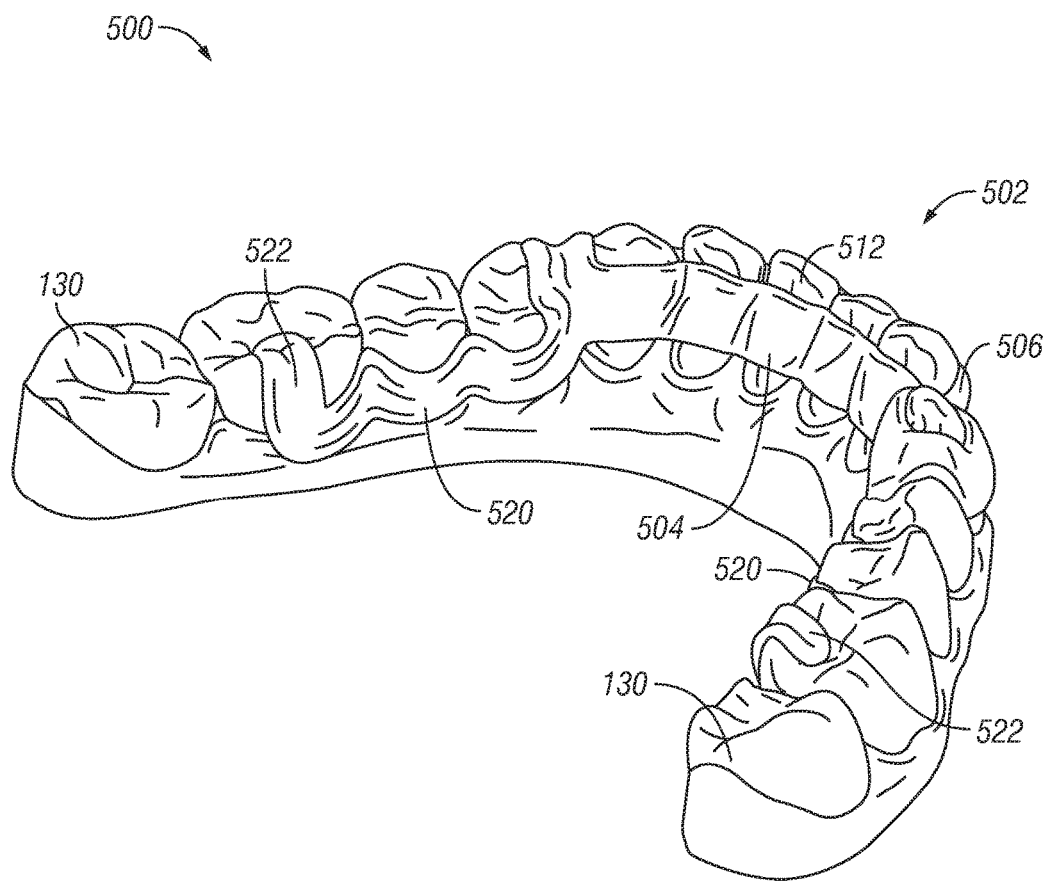
FIG. 12 illustrates an example removable dental appliance providing exposed occlusal surfaces when worn by a patient, the example removable dental appliance relying on three posterior teeth in each quadrant of the mouth for anchorage by bracing against portions of the lingual and occlusal surfaces of the teeth.

FIG. 12 illustrates an example removable dental appliance 500 providing exposed occlusal surfaces when worn by a patient, the example removable dental appliance 500 including anchors configured to mate with the lingual side of posterior teeth of the patient. FIG. 12 further illustrates a 3D digital model of removable dental appliance 500 in combination with 3D digital model 130 of the teeth of a patient. Removable dental appliance 500 may be substantially similar to removable dental appliance 100 (FIG. 4A-5B) with the exception of the configuration of anchors 520. For sake of brevity, details of removable dental appliance 500 that are the same or similar to details previously described with respect to removable dental appliance 100 are described in limited or no detail with respect to removable dental appliance 500.

Removable dental appliance 500 is configured to expose occlusal surfaces of the teeth of a patient when worn by the patient. Removable dental appliance 500 includes appliance body 502. Appliance body 502 forms active band 512, which is configured to surround two or more teeth of the patient. Appliance body 502 includes facial portion 506 and lingual portion 504. Facial portion 506 is configured to register with facial sides of the surrounded teeth, whereas lingual portion 504 is configured to register with lingual sides of the surrounded teeth. As discussed with respect to removable dental appliance 100, facial portion 506 and lingual portion 504 form receptacles configured to accept one of the surrounded teeth when dental appliance 500 is worn by the patient.

Appliance body 502 forms active band 512, which includes facial portion 506 and lingual portion 504 along an anterior portion of appliance body 502. Active band 512 is configured such that occlusal surfaces of the surrounded teeth of the patient are exposed when removable dental appliance 500 is worn by the patient. For example, as worn by the patient, the surrounded teeth are positioned within the receptacles of appliance body 502.

In order to facilitate positioning of the teeth of the patient, at least one of the receptacles may be misaligned as compared to the corresponding tooth of the patient. In this manner, appliance body 502 may be configured to apply rotational and/or translational forces to the corresponding tooth of the patient when removable dental appliance 500 is worn by the patient. In some particular examples, appliance body 502 may be configured to provide only compressive or linear forces. In the same or different examples, appliance body 502 may be configured to apply translational forces to one or more of the teeth within the receptacles.

Removable dental appliance 500 further includes anchors 520. Anchors 520 extend from each side of appliance body 502. Each of anchors 520 includes a hook 522 configured to engage a posterior tooth of the patient. In some examples, the posterior teeth may include a premolar or a molar of the patient. When removable dental appliance 500 is worn by the patient with the surrounded teeth positioned within the receptacles of appliance body 502, the posterior teeth are engaged by hooks 522 of anchors 520. Anchors 520 are configured such that occlusal surfaces of the accepted posterior teeth of the patient remain exposed when removable dental appliance 500 is seated on the patient's dental arch.

Removable dental appliance 500 may function as a spring aligner in that lingual portion 504 of appliance body 502 may be configured to apply force in a generally anterior direction to one or more of the surrounded teeth. Meanwhile, anchors 520 are configured to support the application of the force in the generally anterior direction by lingual portion 504 of appliance body 502 by applying forces in a generally posterior direction to the accepted posterior teeth when removable dental appliance 500 is worn by the patient.

Figure 13A:
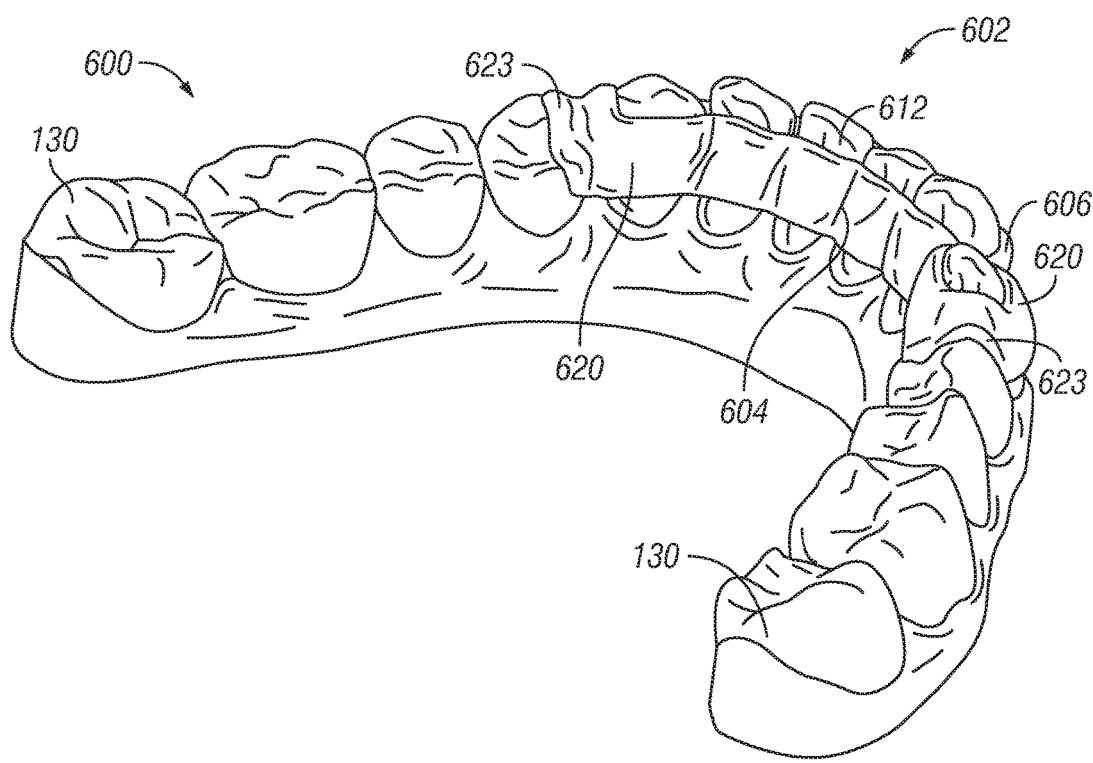
FIGS. 13A and 13B illustrate an example removable dental appliance providing exposed occlusal surfaces when worn by a patient, the example removable dental appliance relying on the cuspids for anchorage by partially surrounding the teeth.
Figure 13B:
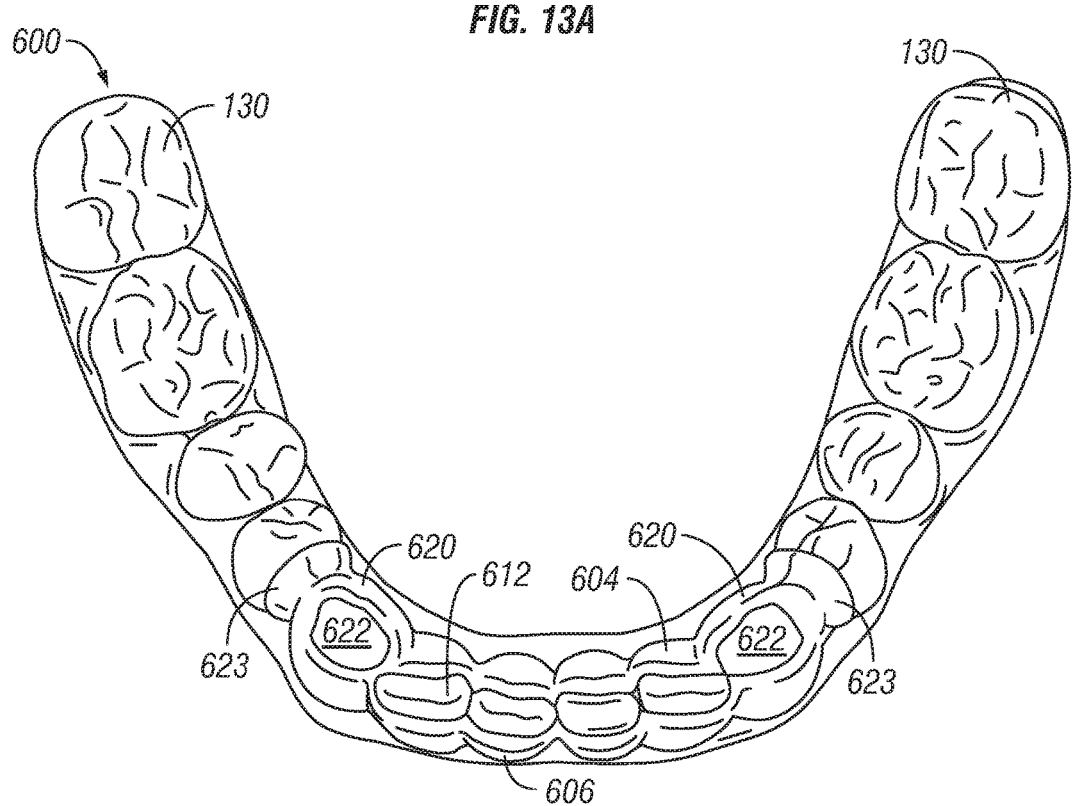

FIGS. 13A and 13B illustrate an example removable dental appliance providing exposed occlusal surfaces when worn by a patient, the example removable dental appliance including anchors configured to accept canine teeth of the patient. FIGS. 13A and 13B further illustrate a 3D digital model of removable dental appliance 500 in combination with 3D digital model 130 of the teeth of a patient. Removable dental appliance 600 may be substantially similar to removable dental appliance 100 (FIG. 4A-5B) with the exception of the configuration of anchors 620. For brevity, details of removable dental appliance 600 that are the same or similar to details previously described with respect to removable dental appliance 100 are described in limited or no detail with respect to removable dental appliance 600.

Removable dental appliance 600 is configured to expose occlusal surfaces of the teeth of a patient when worn by the patient. Removable dental appliance 600 includes appliance body 602. Appliance body 602 forms active band 612, which is configured to surround two or more teeth of the patient. Appliance body 602 includes facial portion 606 and lingual portion 604. Facial portion 606 is configured to register with facial sides of the surrounded teeth, whereas lingual portion 604 is configured to register with lingual sides of the surrounded teeth. As discussed with respect to removable dental appliance 100, facial portion 606 and lingual portion 604 form receptacles configured to accept one of the surrounded teeth when dental appliance 600 is worn by the patient.

Appliance body 602 forms active band 612, which includes facial portion 606 and lingual portion 604 along an anterior portion of appliance body 602. Active band 612 is configured such that occlusal surfaces of the surrounded teeth of the patient are exposed when removable dental appliance 600 is worn by the patient. For example, as worn by the patient, the surrounded teeth are positioned within the receptacles of appliance body 602.

In order to facilitate positioning of the teeth of the patient, at least one of the receptacles may be misaligned as compared to the corresponding tooth of the patient. In this manner, appliance body 602 may be configured to apply rotational and/or translational forces to the corresponding tooth of the patient when removable dental appliance 600 is worn by the patient. In some particular examples, appliance body 602 may be configured to provide only compressive or liner forces. In the same or different examples, appliance body 602 may be configured to apply translational forces to one or more of the teeth within the receptacles.

Removable dental appliance 600 further includes anchors 620. Anchors 620 directly extend from each side of appliance body 602. Each of anchors 620 includes a receptacle 622 configured to accept a canine tooth of the patient. When removable dental appliance 600 is worn by the patient with the surrounded teeth positioned within the receptacles of appliance body 602, the canine teeth are positioned within receptacles 622 of anchors 620. Anchors 620 are configured such that occlusal surfaces of the accepted posterior teeth of the patient remain exposed when removable dental appliance 600 is seated on the patient's dental arch.

Removable dental appliance 600 may function as a spring aligner in that lingual portion 604 of appliance body 602 may be configured to apply force in a generally anterior direction to one or more of the surrounded teeth. Meanwhile, anchors 620 are configured to support the application of the force in the generally anterior direction by lingual portion 604 of appliance body 602 by applying forces in a generally posterior direction to the accepted canine teeth when removable dental appliance 600 is worn by the patient. Like prior examples, removal dental appliance 600 may be adapted to encircle posterior teeth or both posterior and anterior teeth.

Figure 14A:
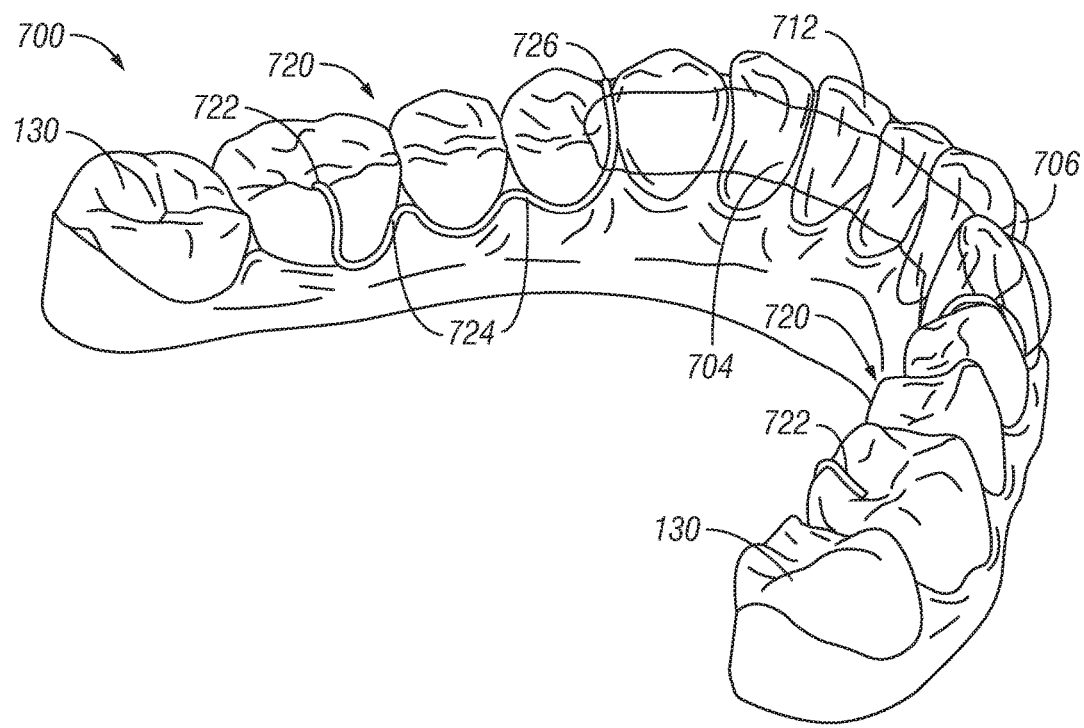
FIGS. 14A and 14B illustrate an example removable dental appliance providing exposed occlusal surfaces when worn by a patient, the example removable dental appliance relying on three posterior teeth in each quadrant of the mouth for anchorage by using metal wires as bracing against portions of the lingual and occlusal surfaces of the teeth.
Figure 14B:
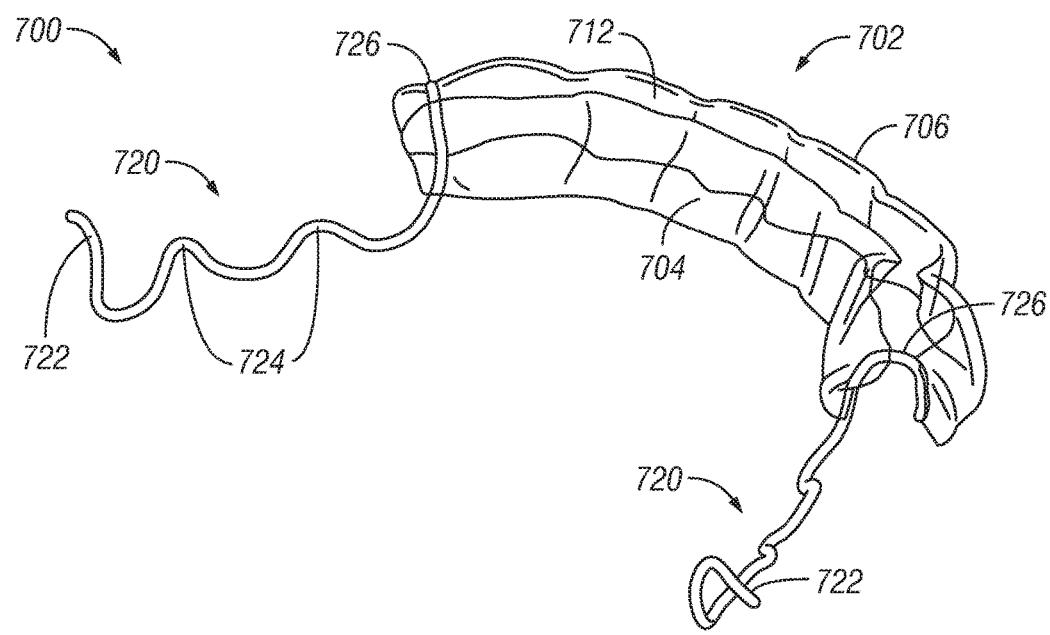

FIGS. 14A and 14B illustrate an example removable dental appliance providing exposed occlusal surfaces when worn by a patient, the example removable dental appliance including wire anchors. FIG. 14A further illustrates a 3D digital model of removable dental appliance 700 in combination with 3D digital model 130 of the teeth of a patient. Removable dental appliance 700 may be substantially similar to removable dental appliance 100 (FIG. 4A-7B) with the exception of the configuration of anchors 720. For brevity, details of removable dental appliance 700 that are the same or similar to details previously described with respect to removable dental appliance 100 are described in limited or no detail with respect to removable dental appliance 700.

Removable dental appliance 700 is configured to expose occlusal surfaces of the teeth of a patient when worn by the patient. Removable dental appliance 700 includes appliance body 702. Appliance body 702 forms active band 712, which is configured to surround two or more teeth of the patient. Appliance body 702 includes facial portion 706 and lingual portion 704. Facial portion 706 is configured to register with facial sides of the surrounded teeth, whereas lingual portion 704 is configured to register with lingual sides of the surrounded teeth. As discussed with respect to removable dental appliance 100, facial portion 706 and lingual portion 704 form receptacles configured to accept one of the surrounded teeth when dental appliance 700 is worn by the patient.

Appliance body 702 forms active band 712, which includes facial portion 706 and lingual portion 704 along an anterior portion of appliance body 702. Active band 712 is configured such that occlusal surfaces of the surrounded teeth of the patient are exposed when removable dental appliance 700 is worn by the patient. For example, as worn by the patient, the surrounded teeth are positioned within the receptacles of appliance body 702.

In order to facilitate positioning of the teeth of the patient, at least one of the receptacles may be misaligned as compared to the corresponding tooth of the patient. In this manner, appliance body 702 may be configured to apply rotational and/or translational forces to the corresponding tooth of the patient when removable dental appliance 700 is worn by the patient. In some particular examples, appliance body 702 may be configured to provide only compressive or liner forces. In the same or different examples, appliance body 702 may be configured to apply translational forces to one or more of the teeth within the receptacles.

Removable dental appliance 700 further includes anchors 720. Anchors 720 extend from each side of appliance body 702. Each of anchors 720 includes a hook 722 configured to engage a portion, typically a cusp, of posterior tooth of the patient. In some examples, the posterior teeth may include a premolar or a molar of the patient. When removable dental appliance 700 is worn by the patient with the surrounded teeth positioned within the receptacles of appliance body 702, the posterior teeth are engaged by hooks 722 of anchors 720. Anchors 720 are configured such that occlusal surfaces of the accepted posterior teeth of the patient remain exposed when removable dental appliance 700. In different examples, hooks 722 may be bent using a computerized manufacturing system or manually by a clinician to conform to the teeth and mouth of a patient.

In contrast to the previously described removable dental appliances, anchors 720 may be formed from a metal wire. In particular, each of anchors 720 includes a proximal portion 724 that connects to appliance body 702. In different examples, appliance body 702 may be overmolded on the proximal portions 726 of anchors 720 or proximal portions 726 may be fastened directly to appliance body 702, for example, by gluing or other bonding technique. Other suitable techniques for fastening anchors 720 to appliance body 702 may also be used.

Anchors 720 may provide stiffness to appliance body 702, which may be formed from a polymeric material as described herein. In the particular example of removable dental appliance 700, the proximal portions 726 of anchors 720 connect lingual portion 704 and facial portion 706 of appliance body 702, and lingual portion 704 and facial portion 706 of appliance body 702 are otherwise separated. In other examples, lingual portion 704 and facial portion 706 of appliance body 702 may connect to one another as with the other removable dental appliances described herein.

Anchors 720 further include central portions 724, which may be bent to follow the gumline of a patient, both to more securely hold removable dental appliance 700 in place and to limit the intrusion into a patient's mount when removable dental appliance 700 is worn by the patient as compared to straight portions. In different examples, central portions 724 may be bent using a computerized manufacturing system or manually by a clinician to conform to the teeth and mouth of a patient. In some examples, any portion of anchors 720 may be formed using a CNC wire-bending machine based on the digital model 130 of the dental structure of the patient. In other examples, the wire portions may be formed using a CNC laser cutting machine.

Removable dental appliance 700 may function as a spring aligner in that lingual portion 704 of appliance body 702 may be configured to apply force in a generally anterior direction to one or more of the surrounded teeth. Meanwhile, anchors 720 are configured to support the application of the force in the generally anterior direction by lingual portion 704 of appliance body 702 by applying forces in a generally posterior direction to the accepted posterior teeth when removable dental appliance 700 is worn by the patient.

Figure 15A:
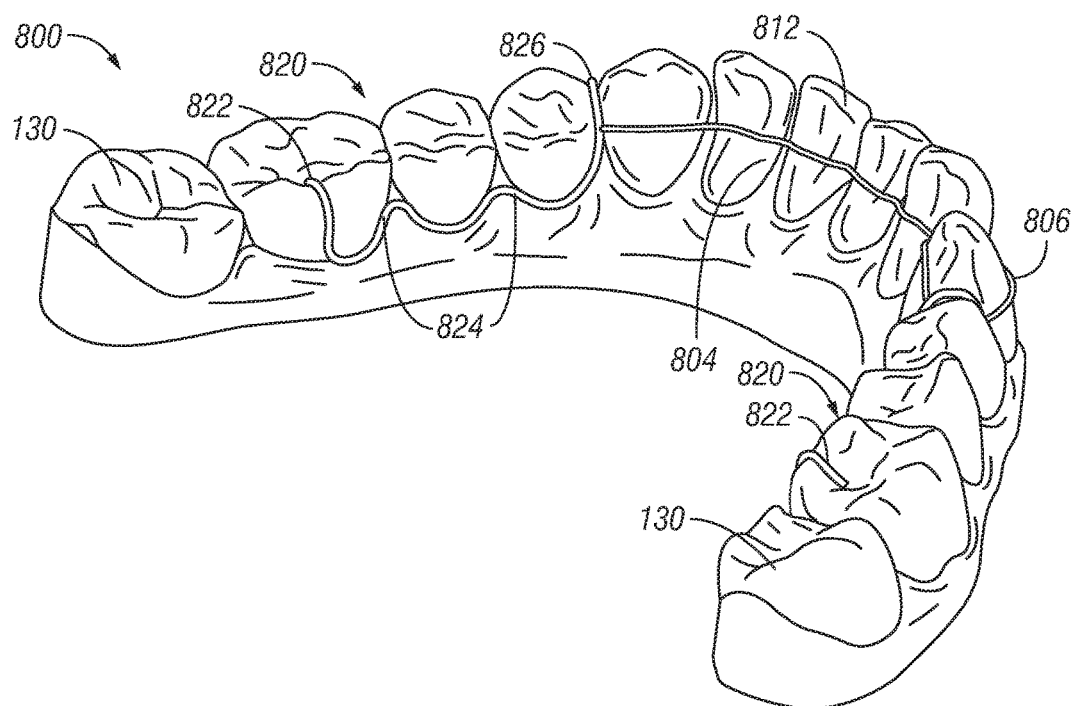
FIGS. 15A and 15B illustrate an example removable dental appliance providing exposed occlusal surfaces when worn by a patient, the example removable dental appliance including an active band formed by metal wires and relying on three posterior teeth in each quadrant of the mouth for anchorage by using metal wires as bracing against portions of the lingual and occlusal surfaces of the teeth.
Figure 15B:
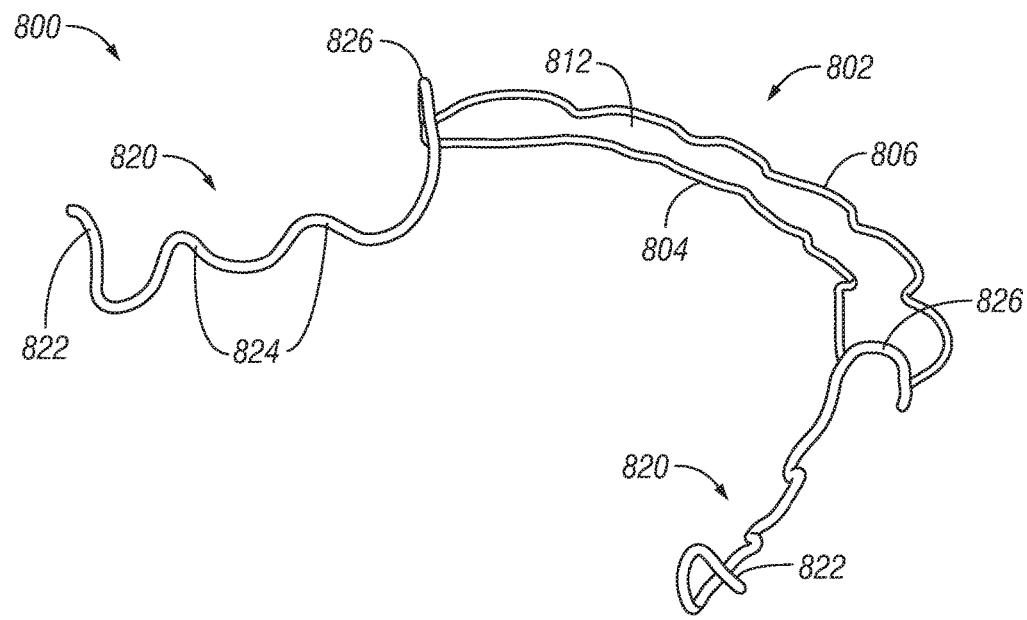

FIGS. 15A and 15B illustrate an example removable dental appliance providing exposed occlusal surfaces when worn by a patient, the example removable dental appliance including wire active band 812 and wire anchors 820. FIG. 15A further illustrates a 3D digital model of removable dental appliance 800 in combination with 3D digital model 130 of the teeth of a patient. Removable dental appliance 800 may be substantially similar to removable dental appliance 700 (FIGS. 14A and 14B) with the exception of the configuration of wire active band 812. For brevity, details of removable dental appliance 800 that are the same or similar to details previously described with respect to removable dental appliance 100 are described in limited or no detail with respect to removable dental appliance 800.

Removable dental appliance 800 is configured to expose occlusal surfaces of the teeth of a patient when worn by the patient. Removable dental appliance 800 includes appliance body 802. Appliance body 802 forms wire active band 812, which is configured to surround two or more teeth of the patient. Appliance body 802 includes facial portion 806 and lingual portion 804. Facial portion 806 is configured to register with facial sides of the surrounded teeth, whereas lingual portion 804 is configured to register with lingual sides of the surrounded teeth. As discussed with respect to removable dental appliance 700 and removable dental appliance 100, facial portion 806 and lingual portion 804 form receptacles configured to accept one of the surrounded teeth when dental appliance 800 is worn by the patient.

Appliance body 802 forms wire active band 812, which includes facial portion 806 and lingual portion 804 along an anterior portion of appliance body 802. Wire active band 812 is configured such that occlusal surfaces of the surrounded teeth of the patient are exposed when removable dental appliance 800 is worn by the patient 800. For example, as worn by the patient, the surrounded teeth are positioned within the receptacles of appliance body 802.

In order to facilitate positioning of the teeth of the patient, at least one of the receptacles may be misaligned as compared to the corresponding tooth of the patient. In this manner, appliance body 802 may be configured to apply rotational and/or translational forces to the corresponding tooth of the patient when removable dental appliance 800 is worn by the patient. In some particular examples, appliance body 802 may be configured to provide only compressive or liner forces. In the same or different examples, appliance body 802 may be configured to apply translational forces to one or more of the teeth within the receptacles.

Removable dental appliance 800 further includes anchors 820. Anchors 820 extend from each side of appliance body 802. Each of anchors 820 includes a hook 822 configured to engage a posterior tooth of the patient. In some examples, the posterior teeth may include a premolar or a molar of the patient. When removable dental appliance 800 is worn by the patient with the surrounded teeth positioned within the receptacles of appliance body 802, the posterior teeth are engaged by hooks 822 of anchors 820. Anchors 820 are configured such that occlusal surfaces of the accepted posterior teeth of the patient remain exposed when removable dental appliance 800. In different examples, hooks 822 may be bent using a computerized manufacturing system or manually by a clinician to conform to the teeth and mouth of a patient.

In contrast to the previously described removable dental appliances, active band 812, including facial portion 806 and lingual portion 804, as well as each of anchors 820, may be formed from a metal wire. In particular, each of anchors 820 includes a proximal portion 826 that connects to appliance body 802. In some examples, any portion of dental appliance 800, such as active band 812, including facial portion 806 and lingual portion 804, as well as each of anchors 820 may be formed using a CNC wire-bending machine based on the digital model 130 of the dental structure of the patient.

In the particular example of removable dental appliance 800, the proximal portions 826 of anchors 820 connect lingual portion 804 and facial portion 806 of appliance body 802, and lingual portion 804 and facial portion 806 of appliance body 802 are otherwise separated. In other examples, lingual portion 804 and facial portion 806 of appliance body 802 may connect to one another as with the other removable dental appliances described herein.

Anchors 820 further include central portions 824, which may be bent to follow the gumline of a patient, both to more securely hold removable dental appliance 800 in place and to limit the intrusion into a patient's mount when removable dental appliance 800 is worn by the patient as compared to straight portions. In different examples, central portions 824 may be bent using a computerized manufacturing system or manually by a clinician to conform to the teeth and mouth of a patient.

Removable dental appliance 800 may function as a spring aligner in that lingual portion 804 of appliance body 802 may be configured to apply force in a generally anterior direction to one or more of the surrounded teeth. Meanwhile, anchors 820 are configured to support the application of the force in the generally anterior direction by lingual portion 804 of appliance body 802 by applying forces in a generally posterior direction to the accepted posterior teeth when removable dental appliance 800 is worn by the patient.

Various techniques of this disclosure may be implemented in a wide variety of computer devices, such as servers (including the Cloud), laptop computers, desktop computers, notebook computers, tablet computers, hand-held computers, smart phones, and the like. Any components, modules or units have been described to emphasize functional aspects and does not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Various examples have been described. These and other examples are within the scope of the following claims.

Embodiments

1. A method comprising: receiving, with a computer system, a digital representation of a three-dimensional (3D) tooth structure of a patient, the tooth structure providing initial positions of one or more teeth of the patient; determining, with the computer system, dimensions and shapes of a removable dental appliance for the patient, the dimensions and shapes of the removable dental appliance being configured to reposition the one or more teeth of the patient from their initial positions to adjusted positions when the removable dental appliance is worn by the patient; and transmitting, with the computer system, a representation of the removable dental appliance to a computer-aided manufacturing system, wherein the removable dental appliance comprises an appliance body configured to surround two or more teeth of the patient, wherein the appliance body an active band and at least one anchor includes: a facial portion configured to register with facial sides of the surrounded teeth; and a lingual portion configured to register with lingual sides of the surrounded teeth, wherein the appliance body is configured such that occlusal surfaces of the surrounded teeth of the patient are exposed when the removable dental appliance is worn by the patient.

2. The method of embodiment 1, wherein the three-dimensional (3D) dental structure of the patient further includes at least some portion of tooth roots, gingiva, periodontal ligaments (PDL), alveolar bone, or cortical bone.

3. The method of any of the previous embodiments, wherein the facial portion and lingual portion cooperate to form an active band, and wherein the band comprises one or more receptacles for receipt of the surrounded teeth.

4. The method of any of embodiments 1-3, wherein determining, with the computer, dimensions and shapes of a removable dental appliance includes accepting input from a user, wherein said input influences at least one of said dimensions and shapes.

5. The method of any of embodiments 1-3, wherein determining, with the computer, dimensions and shapes of a removable dental appliance includes automatically determining at least one of said dimensions and shapes.

6. The method of any of embodiments 1-5, wherein determining, with the computer, dimensions and shapes of a removable dental appliance includes presenting a representation of the removable dental appliance to a user for review.

7. The method of any of embodiments 1-6, wherein transmitting the representation of the removable dental appliance includes sending a digital model of the removable dental appliance from the computer system to the computer-aided manufacturing system, and manufacturing at least a portion of the removable dental appliance with the computer-aided manufacturing system according to the digital model from the computer system.

8. The method of any of embodiments 1-7, wherein the computer-aided manufacturing system includes a 3D printer, and wherein at least a portion of the dental appliance is formed using the 3D printer.

9. The method of embodiment 8, wherein the facial portion of the appliance body and the lingual portion of the appliance body form receptacles, wherein each receptacle is configured to accept at least one of the surrounded teeth, and wherein forming shapes of the receptacles of the appliance body includes printing the surfaces of the appliance body that form the receptacles with the 3D printer.

10. The method of any of embodiments 1-7, wherein the computer-aided manufacturing system includes a CNC wire-bending machine, and wherein at least a portion of the dental appliance is formed using the CNC wire-bending machine.

11. The method of any of embodiments 1-7 and 10, wherein the manufacturing system includes a CNC milling machine, and wherein at least a portion of the dental appliance is formed using the CNC milling machine.

12. The method of any of embodiments 1-7 and 10, wherein the manufacturing system includes a CNC laser cutting machine, and wherein at least a portion of the dental appliance is formed using the CNC laser cutting machine.

13. The method of embodiment 12, wherein the CNC laser cutting machine is configured to vary the depth of cut along its cut path to facilitate forming the at least some portion of the dental appliance.

14. The method of any of embodiments 1-13, further comprising: determining, with the computer system, dimensions and shapes of each of an ordered set of a removable dental appliances for the patient, the removable dental appliance being one of the ordered set of removable dental appliances for the patient, wherein each removable dental appliance in the ordered set of removable dental appliances is configured to incrementally reposition the teeth of the patient to a more advanced position than any one of the earlier removable dental appliances within the set of the removable dental appliances.

15. The method of any of embodiment 14, wherein determining, with the computer system, dimensions and shapes of the removable dental appliance includes selecting, with the computer system, the dimensions and shapes of the removable dental appliance according to a set of predefined design constraints, the set of predefined design constraints including one or more of a group consisting of: a maximum localized force applied to one or more of the surrounded teeth; a maximum rotational force applied to one or more of the surrounded teeth; a maximum translational force applied to one or more of the surrounded teeth; a maximum total force applied to one or more of the surrounded teeth; and a maximum strain applied to the removable dental appliance when worn by the patient when the surrounded teeth are in their initial positions.

16. The method of any of embodiment 15, further comprising selecting, with the computer system, a material of the removable dental appliance.

17. The method of any of embodiments 1-16, wherein determining, with the computer system, dimensions and shapes of the removable dental appliance includes selecting thicknesses of the facial portion and the lingual portion of the appliance body in order to provide a stiffness suitable to reposition the one or more teeth of the patient from their initial positions to adjusted positions when the removable dental appliance is worn by the patient.

18. The method of any of embodiments 1-17, wherein the facial portion of the appliance body and the lingual portion of the appliance body form receptacles, wherein each receptacle is configured to accept at least one of the surrounded teeth, and wherein at least one of the receptacles in the appliance body is aligned as compared to the corresponding tooth of the patient such that the appliance body is configured to apply rotational forces to the corresponding tooth of the patient when the removable dental appliance is worn by the patient.

19. The method of embodiment 18, wherein the rotational forces applied to the one or more teeth of the patient result from one or more couples formed between opposing surfaces of the facial and lingual portions of the appliance body and the surrounded teeth.

20. The method of embodiment 18, wherein the rotational forces applied to the one or more teeth of the patient result from one or more couples formed between interior surfaces of the facial and lingual portions of the appliance body and roots of one or more corresponding teeth.

21. The method of any of embodiments 1-20, wherein at least a portion of the dental appliance is configured to apply translational forces to one or more teeth when the removable dental appliance is worn by the patient.

22. The method of embodiment 21, wherein the translational forces applied to the one or more teeth of the patient result from one or more compression points between interior surfaces of the facial and lingual portions of the appliance body and the one or more contacted teeth.

23. The method of embodiment 21, wherein the translational forces applied to the one or more teeth of the patient result from one or more tension points between interior surfaces of the facial and lingual portions of the appliance body and one or more separate appliances which are attached directly to the dental structure of the patient.

24. The method of any of embodiments 1-23, wherein the removable dental appliance further comprises one or more anchors extending from a side of the appliance body.

25. The method of any of embodiments 1-23, wherein the surrounded teeth are anterior teeth of the patient.

26. The method of embodiment 25, wherein the surrounded teeth are a first set of surrounded teeth, the removable dental appliance further including an band configured to surround a second set of teeth of the patient, the second set of teeth of the patient being directly adjacent to the first set of surrounded teeth.

27. The method of any of embodiments 1-26, wherein the facial and lingual portions form an active band of the removable dental appliance, and wherein the appliance further comprises one or more struts connected to the active band.

28. The method of embodiment 27, wherein the removable dental appliance further comprises anchors extending from each side of the appliance body, and wherein the struts couple the active band to the anchors.

29. The method of embodiment 28, wherein the removable dental appliance further comprises of one or more additional bands connected to the distal ends of the one or more struts.

30. The method of embodiment 29, wherein the one or more struts span one or more intermediate teeth.

31. The method of embodiment 29, wherein the one or more struts span one or more gaps between the surrounded teeth.

32. The method of embodiment 28, wherein at least one of the removable dental appliances incorporates a pontic.

34. The method of any of embodiments 1-32, wherein the removable dental appliance further comprises a strut along a plurality of anterior teeth, said struts connected to anchor bands at distal ends of the brace.

35. The method of any of embodiments 1-34, wherein determining, with the computer system, dimensions and shapes of the removable dental appliance includes modifying the tooth structure providing initial positions of one or more teeth of the patient to produce a modified tooth structure, wherein in the dimensions and shapes of the removable dental appliance conform to the modified tooth structure.

36. The method of embodiment 35, wherein the modified tooth structure represents an incremental repositioning of the one or more teeth of the patient as compared to the initial positions of the one or more teeth of the patient.

37. The method of any of embodiments 1-36, further comprising presenting, with the computer, a representation of the removable dental appliance to a user.

38. The method of any of embodiments 1-37, wherein the computer system includes a plurality of computing devices operably connected via one or more computer networks.

39. A computer-readable storage medium that stores computer system-executable instructions that, when executed, configure a processor to perform the method of any of embodiments 1-38.

40. A computer-readable storage medium that stores computer system-executable instructions that, when executed, configure a processor to: receive a digital representation of a three-dimensional (3D) tooth structure of a patient, the tooth structure providing initial positions of one or more teeth of the patient; determine dimensions and shapes of a removable dental appliance for the patient, the dimensions and shapes of the removable dental appliance being configured to reposition the one or more teeth of the patient from their initial positions to adjusted positions when the removable dental appliance is worn by the patient; and transmit a representation of the removable dental appliance to a computer-aided manufacturing system, wherein the removable dental appliance comprises an appliance body configured to surround two or more teeth of the patient, wherein the appliance body includes: a facial portion configured to register with facial sides of the surrounded teeth; and a lingual portion configured to register with lingual sides of the surrounded teeth, wherein the appliance body is configured such that occlusal surfaces of the surrounded teeth of the patient are exposed when the removable dental appliance is worn by the patient.

41. The computer-readable storage medium of embodiment 40, wherein transmitting the representation of the removable dental appliance includes sending a digital model of the removable dental appliance from the computer system to the computer-aided manufacturing system, and manufacturing at least a portion of the removable dental appliance with the computer-aided manufacturing system according to the digital model from the computer system.

42. The computer-readable storage medium of embodiments 40-41, wherein the computer system-executable instructions that, when executed, further configure the processor to: determine dimensions and shapes of each of an ordered set of a removable dental appliances for the patient, the removable dental appliance being one of the ordered set of removable dental appliances for the patient, wherein each removable dental appliance in the ordered set of removable dental appliances is configured to incrementally reposition the teeth of the patient such that the ordered set of removable dental appliances is configured to reposition the teeth of the patient to a more advanced position than any one of the earlier removable dental appliances within the set of the removable dental appliances; and present representations of each of the ordered set of removable dental appliances to the user.

43. The computer-readable storage medium of embodiments 40-42, wherein determining dimensions and shapes of the removable dental appliance includes selecting the dimensions and shapes of the removable dental appliance according to a set of predefined design constraints, the set of predesigned design constraints including one or more of a group consisting of: a maximum localized force applied to one or more of the surrounded teeth; a maximum rotational force applied to one or more of the surrounded teeth; a maximum translational force applied to one or more of the surrounded teeth; a maximum total force applied to one or more of the surrounded teeth; and a maximum strain applied to the removable dental appliance when worn by the patient when the surrounded teeth are in their initial positions.

44. The computer-readable storage medium of embodiment 43, wherein the computer system-executable instructions that, when executed, further configure the processor to select a material of the removable dental appliance.

45. The computer-readable storage medium of any of embodiments 40-44, wherein determining dimensions and shapes of the removable dental appliance includes selecting material properties of the appliance body in order to provide a stiffness suitable to reposition the one or more teeth of the patient from their initial positions to adjusted positions when the removable dental appliance is worn by the patient.

46. The computer-readable storage medium of any of embodiments 40-45, wherein the facial portion of the appliance body and the lingual portion of the appliance body form receptacles, wherein each receptacle is configured to accept at least one of the surrounded teeth, and wherein at least one of the receptacles in the appliance body is aligned as compared to the corresponding tooth of the patient such that the appliance body is configured to apply rotational forces to the corresponding tooth of the patient when the removable dental appliance is worn by the patient.

47. The computer-readable storage medium of any of embodiments 40-46, wherein the removable dental appliance further comprises anchors extending from each side of the appliance body.

48. The computer-readable storage medium of any of embodiments 40-47, wherein the surrounded teeth are anterior teeth of the patient.

49. The computer readable storage medium of embodiment 48, wherein the removable dental appliance further comprises anchors extending from each side of the appliance body, and wherein the anchors extend distally from the appliance body and accept portions of posterior teeth of the patient.

50. A computer system comprising:
one or more databases storing a digital representation of a three-dimensional (3D) tooth structure of a patient, the tooth structure providing initial positions of one or more teeth of the patient; and one or more processors configured to: access the digital representation of the 3D tooth structure; determine dimensions and shapes of a removable dental appliance for the patient, the dimensions and shapes of the removable dental appliance being configured to reposition the one or more teeth of the patient from their initial positions to adjusted future positions when the removable dental appliance is worn by the patient; and transmit a representation of the removable dental appliance to a computer-aided manufacturing system, wherein the removable dental appliance comprises an appliance body configured to surround two or more teeth of the patient, wherein the appliance body includes: a facial portion configured to register with facial sides of the surrounded teeth; and a lingual portion configured to register with lingual sides of the surrounded teeth, wherein the appliance body is configured such that occlusal surfaces of the surrounded teeth of the patient are exposed when the removable dental appliance is worn by the patient.

51. A method comprising: receiving, with a computer system, a digital representation of a three-dimensional (3D) tooth structure of a patient, the tooth structure providing initial positions of one or more teeth of the patient; determining, with the computer system, dimensions and shapes of a removable dental appliance for the patient, the dimensions and shapes of the removable dental appliance being configured to reposition the one or more teeth of the patient from their initial positions to adjusted positions when the removable dental appliance is worn by the patient; and transmitting, with the computer system, a representation of the removable dental appliance to a computer-aided manufacturing system, wherein the removable dental appliance comprises an appliance body configured to engage two or more teeth of the patient and at least one anchor, wherein the appliance body includes either: a facial portion configured to register with facial sides of the surrounded teeth; and a lingual portion configured to register with lingual sides of the surrounded teeth, wherein the appliance body is configured such that occlusal surfaces of the engaged teeth of the patient are exposed when the removable dental appliance is worn by the patient.

52. The method of embodiment 51, wherein the removable dental appliance comprises one or more struts extending in a distal direction from the appliance body.

53. The method of embodiment 52, wherein the struts couple the appliance body to the at least one anchor.

What is claimed is:
1. A method comprising:
receiving, with a computer system, a digital representation of a three-dimensional (3D) tooth structure of a patient, the tooth structure providing initial positions of one or more teeth of the patient;
determining, with the computer system, dimensions and shapes of a removable dental appliance for the patient, the dimensions and shapes of the removable dental appliance being configured to reposition the one or more teeth of the patient from their initial positions to adjusted positions when the removable dental appliance is worn by the patient; and transmitting, with the computer system, a representation of the removable dental appliance to a computer-aided manufacturing system, wherein the removable dental appliance comprises an appliance body configured to surround two or more teeth of the patient, wherein the appliance body having an active band and at least one anchor includes:

a facial portion configured to register with facial sides of the surrounded teeth; and a lingual portion configured to register with lingual sides of the surrounded teeth, wherein the appliance body is configured such that occlusal surfaces of the surrounded teeth of the patient are exposed when the removable dental appliance is worn by the patient, wherein the facial and lingual portions form an active band of the removable dental appliance, and wherein the appliance further comprises one or more struts connected to the active band, wherein the removable dental appliance further comprises anchors extending from each side of the appliance body, and wherein the struts couple the active band to the anchors.

2. The method of claim 1, wherein the facial portion and lingual portion cooperate to form an active band, and wherein the band comprises one or more receptacles for receipt of the surrounded teeth.

3. The method of claim 1, wherein determining, with the computer, dimensions and shapes of a removable dental appliance includes accepting input from a user, wherein said input influences at least one of said dimensions and shapes.

4. The method of claim 1, wherein determining, with the computer, dimensions and shapes of a removable dental appliance includes automatically determining at least one of said dimensions and shapes.

5. The method of claim 1, wherein transmitting the representation of the removable dental appliance includes sending a digital model of the removable dental appliance from the computer system to the computer-aided manufacturing system, and manufacturing at least a portion of the removable dental appliance with the computer-aided manufacturing system according to the digital model from the computer system.

6. The method of claim 1,
wherein the computer-aided manufacturing system includes a 3D printer, and
wherein at least a portion of the dental appliance is formed using the 3D printer.

7. The method of claim 6,
wherein the facial portion of the appliance body and the lingual portion of the appliance body form receptacles, wherein each receptacle is configured to accept at least one of the surrounded teeth, and
wherein forming shapes of the receptacles of the appliance body includes printing the surfaces of the appliance body that form the receptacles with the 3D printer.

8. The method of claim 1, further comprising:
determining, with the computer system, dimensions and shapes of each of an ordered set of a removable dental appliances for the patient, the removable dental appliance being one of the ordered set of removable dental appliances for the patient,
wherein each removable dental appliance in the ordered set of removable dental appliances is configured to incrementally reposition the teeth of the patient to a more advanced position than any one of the earlier removable dental appliances within the set of the removable dental appliances.

9. The method of claim 1, wherein determining, with the computer system, dimensions and shapes of the removable dental appliance includes selecting, with the computer system, the dimensions and shapes of the removable dental appliance according to a set of predefined design constraints, the set of predefined design constraints including one or more of a group consisting of:

a maximum localized force applied to one or more of the surrounded teeth;

a maximum rotational force applied to one or more of the surrounded teeth;

a maximum translational force applied to one or more of the surrounded teeth;

a maximum total force applied to one or more of the surrounded teeth; and a maximum strain applied to the removable dental appliance when worn by the patient when the surrounded teeth are in their initial positions.

10. The method of claim 9, further comprising selecting, with the computer system, a material of the removable dental appliance.

11. The method of claim 1, wherein determining, with the computer system, dimensions and shapes of the removable dental appliance includes selecting thicknesses of the facial portion and the lingual portion of the appliance body in order to provide a stiffness suitable to reposition the one or more teeth of the patient from their initial positions to adjusted positions when the removable dental appliance is worn by the patient.

12. The method of claim 1,
wherein the facial portion of the appliance body and the lingual portion of the appliance body form receptacles, wherein each receptacle is configured to accept at least one of the surrounded teeth, and
wherein at least one of the receptacles in the appliance body is aligned as compared to the corresponding tooth of the patient such that the appliance body is configured to apply rotational forces to the corresponding tooth of the patient when the removable dental appliance is worn by the patient.

13. The method of claim 1, wherein at least a portion of the dental appliance is configured to apply translational forces to one or more teeth when the removable dental appliance is worn by the patient.

14. The method of claim 1, wherein the surrounded teeth are anterior teeth of the patient.

15. The method of claim 14, wherein the surrounded teeth are a first set of surrounded teeth, the removable dental appliance further including a band configured to surround a second set of teeth of the patient, the second set of teeth of the patient being directly adjacent to the first set of surrounded teeth.

16. The method of claim 1, wherein the removable dental appliance further comprises of one or more additional bands connected to the distal ends of the one or more struts.

17. The method of claim 1, wherein determining, with the computer system, dimensions and shapes of the removable dental appliance includes modifying the tooth structure providing initial positions of one or more teeth of the patient to produce a modified tooth structure, wherein in the dimensions and shapes of the removable dental appliance conform to the modified tooth structure.

* * * * *